US006761692B2

(12) United States Patent
Angelsen et al.

(10) Patent No.: US 6,761,692 B2
(45) Date of Patent: Jul. 13, 2004

(54) HIGH FREQUENCY AND MULTI FREQUENCY BAND ULTRASOUND TRANSDUCERS BASED ON CERAMIC FILMS

(75) Inventors: Bjorn A. J. Angelsen, Trondheim (NO); Tonni F. Johansen, Trondheim (NO); Jarle Østgård, Røros (NO)

(73) Assignee: Eagle Ultrasound AS, Trondheim (NO)

( * ) Notice: Subject to any disclaimer, the term of this patent is extended or adjusted under 35 U.S.C. 154(b) by 0 days.

(21) Appl. No.: 10/180,990

(22) Filed: Jun. 24, 2002

(65) Prior Publication Data

US 2003/0023169 A1 Jan. 30, 2003

Related U.S. Application Data

(60) Provisional application No. 60/300,787, filed on Jun. 25, 2001.

(51) Int. Cl.[7] .................................................. A61B 8/00

(52) U.S. Cl. ....................................... 600/459; 310/334

(58) Field of Search ................................ 600/437, 458, 600/459; 310/334–336

(56) References Cited

U.S. PATENT DOCUMENTS 5,329,496 A * 7/1994 Smith ......................... 367/140
5,410,205 A * 4/1995 Gururaja ..................... 310/328
5,625,149 A * 4/1997 Gururaja et al. .............. 73/632
5,825,117 A * 10/1998 Ossmann et al. ........... 310/317
5,938,612 A * 8/1999 Kline-Schoder et al. .... 600/459
6,443,900 B2 * 9/2002 Adachi et al. .............. 600/458
6,645,150 B2 * 11/2003 Angelsen et al. ........... 600/459

* cited by examiner

*Primary Examiner*—Francis J. Jaworski
(74) *Attorney, Agent, or Firm*—Cohen, Pontani, Lieberman & Pavane

(57) ABSTRACT

A design and a manufacturing method of ultrasound transducers based on films of ferro-electric ceramic material is presented, the transducers being particularly useful for operating at frequencies above 10 MHz. The designs also involve acoustic load matching layers that provides particularly wide bandwidth of the transducers, and also multiple electric port transducers using multiple piezoelectric layers, for multi-band operation of the transducers over an even wider band of frequencies that covers ~4 harmonics of a fundamental band. A transceiver drive system for the multi-port transducers that provides simple selection of the frequency bands of transmitted pulses as well as transmission of multi-band pulses, and reception of scattered signals in multiple frequency bands, is presented. The basic designs can be used for elements in a transducer array, that provides all the features of the single element transducer for array steering of the focus and possibly also direction of a pulsed ultrasound beam at high frequencies and multi-band frequencies. The manufacturing technique can involve tape-casting of the ceramic films, deposition of the ceramic films onto a substrate with thick film printing, sol-gel, or other deposition techniques, where manufacturing methods for load matching layers and composite ceramic layers are described.

55 Claims, 19 Drawing Sheets

HIGH FREQUENCY AND MULTI FREQUENCY BAND ULTRASOUND TRANSDUCERS BASED ON CERAMIC FILMS

This application claims priority from U.S. Provisional Patent Application Serial No.: 60/300,787, filed: Jun. 25, 2001.

BACKGROUND OF THE INVENTION

1. Field of the Invention

The present invention is directed to technology and design of efficient ultrasound transducers for high frequencies, and also transducers with multiple electric ports for efficient operation in multiple frequency bands, for example frequency bands with a harmonic relation. The invention has special advantages where the highest frequencies are above 10 MHz, but has also applications for transducers at lower frequencies.

2. Description of the Related Art

Medical ultrasound imaging at frequencies above ~10 MHz, has a wide range of applications for studying microstructures in soft tissues, such as the composition of small tumors or a vessel wall. In many of these situations it is also desirable to use ultrasound pulses with frequencies in several frequency bands, for example to 1. use a pulse with frequencies in a low frequency band of for example 30–40 MHz to get larger image depth for an overview image, and then be able to switch to or use simultaneously a pulse with frequencies in a high frequency band, say 60–80 MHz, for high resolution imaging of close structures in a shorter depth of the image, or
2. to transmit an ultrasound pulse with frequencies in a low frequency band, say around 30 MHz, and receive back scattered signal components at a harmonic of the transmit band, say a $2^{nd}$ harmonic band around 60 MHz, a $3^{rd}$ harmonic band around 90 MHz, or even a sub-harmonic band around 15 MHz.

Ultrasound transducers for medical applications are currently based on ferro-electric, ceramic plates as the active material, that vibrates in thickness mode. When polarized, the materials show piezoelectric properties with efficient electromechanical coupling. However, the characteristic impedance of the ceramic material ($Z_x$~33 MRayl) is much higher than that of the tissue load material ($Z_L$~1.5 Rayl). In order to get adequate thickness vibration amplitude of the plate for efficient power coupling into the tissue load material, one must operate the plates at thickness resonance, typically $L_x=\lambda/2$ resonance. Here $L_x$ is the plate thickness, $\lambda=c_1/f$ is the wavelength of longitudinal waves normal to the plate with wave velocity $c_1$ and frequency f. The resonance makes the transducer efficient in a band of frequencies around a center frequency $f_0=c_1/\lambda_0=c_1/2L_x$. Acoustic matching plates between the ceramic plate and the load are used to improve the power coupling to the load, a technique that increases the bandwidth of the transducer resonance.

With the well known composite technique, where the ceramic plate is diced into small posts, and the interpost space is filled with epoxy, the efficient characteristic impedance is reduced to ~15 MRayl, which is still around 10 times higher than the characteristic impedance of the load, such as soft tissue or water. Transducers of composite material must therefore also operate in thickness resonant mode, albeit one can obtain some wider bandwidth than with the transducers of whole ceramic.

Hence, both with whole and composite ceramic, the resonant operation requires that the plate thickness is inversely proportional to the center frequency of the operating transducer band.

This requires thicknesses in the range of 200–20 μm for center frequencies in the range of 10–100 MHz. Today, lapping of the ceramic plate is the common technology to manufacture plates with correct thickness, which becomes difficult and expensive at thicknesses in ranges below 50–60 μm, corresponding to frequencies above 30–40 MHz. Composite ceramic/epoxy material is also difficult to make for frequencies above 15 MHz, and it is hence a general need for efficient methods to manufacture transducers with a functioning high frequency band above 15 MHz.

SUMMARY OF THE INVENTION

The invention presents a new design of ultrasound transducers where the active electromechanical coupling material is ferroelectric, ceramic films that are made piezoelectric through electric polarization. The piezoelectric film layers are arranged into a transducer plate composed of multiple film layers, possibly also non-piezoelectric layers, where all the film layers have close to the same characteristic impedance. For coupling of the vibrations to an electric port, electrodes are placed inside the plate structure with a piezoelectric layer between the electrodes to form an electric port of the transducer, which interacts with the acoustic port of the transducer plate surface. By placing the electrodes inside the plate, the distance between the electrodes can be made substantially shorter than the total thickness of the transducer plate, which is an important aspect for high frequency operation of the transducer according to the invention.

The electromechanical coupling of the electrode port is highest at the frequencies where the thickness vibrations of the piezoelectric layer between the electrodes, is maximum. Due to reflections inside the transducer, one obtains a standing wave vibration pattern within the plate. The maximal vibration amplitude in the plate is found at the plate resonances, and to transform the resonant vibration amplitude to a large thickness vibration of the material between the electrodes, one must also place the electrodes at antinodes with opposite vibration direction in the standing wave vibration pattern. This gives a distance between the electrodes ~$\lambda/2$, where $\lambda$ is the wave length in the material. Hence, the highest sensitivity of the transducer is found when the transducer plate is at a thickness resonance and the distance between the electrodes is ~$\lambda/2$ with correct placement at antinodes in the standing wave pattern. With very high backing impedance, the back interface is a node, and it can pay to put one electrode at the back interface and the other at the antinode at $\lambda/4$ distance in front of the back electrode.

The close to constant characteristic impedance within the transducer plate implies that the mechanical thickness resonances of the transducer are determined by the total plate thickness, not by the thicknesses of the individual film layers that composes the plate. By placing electrodes inside the transducer plate, the transducer plate can operate over a larger range of resonances, from $\lambda/2$ to multiple $\lambda$ resonances, while the electrodes at the center frequency are placed at antinodes with distance ~$\lambda/2$ internal in the transducer plate, maximizing the electromechanical coupling of the electrodes over the actual frequency band. This allows the use of thicker transducer plates than the standard $\lambda/2$ transducer plates, which provides manufacturing advantages as described below.

The plate is hence so much thicker than the active material between the closest electrode layers, that the phase angle of the wave propagation through the film layers outside these active layers has a substantial, non-negligible effect on the mechanical thickness resonances of the whole plate. We shall say that a layer has a thickness substantially larger than another layer when the difference between the two layers of the wave propagation phase angle is non-negligible in the determination of resonances. Similarly, a layer has non-negligible thickness when the propagation phase angle is non-negligible in the determination of resonances Film layers outside the active ceramic material can be made of other types of material with similar characteristic impedance as the ferroelectric, ceramic film, for example layers of conductive film. Conducting layers can have a combined function as electrodes, and as vibrating layer with non-zero thickness for the definition of the transducer plate thickness resonances. One simple design of the transducer according to the invention, is an active ferroelectric ceramic layer with a thin electrode with negligible propagation phase angle on the back side, and a conducting layer on the front side which both functions as a front electrode and an elastic layer that makes the total plate substantially thicker than the active piezoelectric layer. Such a conducting layer can for example be made as a film of an Ag/Pd mixture. Other examples with more than two electrodes that gives multiple electric ports for multi-band operation of the transducer, is shown in the specification below.

The multi layer structure can be made with tape casting of the films, or deposition onto a substrate with thick film printing, sol-gel deposition, or other deposition techniques. With tape-casting techniques one can typically make films with thickness in the range of ~10–30 $\mu$m. The raw films before sintering are quite pliable, and layers of films can be stacked to form plates of larger thickness. The films are sintered at temperatures ~1000° C., which makes the plate brittle and limits the lower thickness of self-supporting plates and hence the highest operable frequency with ordinary $\lambda/2$ resonant transducer plates made with tape casting techniques. By placing electrodes inside the plate as described, one can obtain efficient electro-acoustic coupling at frequencies where the total plate thickness $L_x$ is substantially larger than $\lambda/2$, allowing increased thicknesses $L_x$ of the total transducer plate that increases the stability during the sintering process and other handling of the plate. The design is specially useful for operating frequencies above ~30 MHz.

With deposition of the ceramic films onto a substrate, one has a problem that many actual substrate materials contaminate the ferroelectric ceramic film during the sintering processes, so that in the neighborhood of the substrate, the film loses its ferroelectric properties, and hence also its piezoelectric properties. Substrates that withstand the sintering process without destruction of the ceramics ferroelectric properties, are rigid so that they produce ringing in the transducer vibrations after the pulse transmission. The invention devises a solution to the contamination problem by using a non-piezoelectric isolation layer between the substrate and the active, piezoelectric, electromechanical coupling layers, with characteristic impedance close to that of the piezoelectric layer. This layer can be made of a ceramic film that is allowed to be contaminated during the sintering process without reducing the transducer function, or other materials, like for example zirconium (Zr) or mixtures of silver (Ag) and palladium (Pd). One can then use substrates, like silicon (Si), that can be etched after the sintering process to such low thickness that the ultrasound can be transmitted through the remnant substrate layer that functions as a load matching layer.

Load matching layers are used for acoustic connection between the transducer plate and the load material to increase the bandwidth of the mechanical resonances of the plate. Manufacturing of load matching layers with correct thickness and characteristic impedance at these high frequencies (i.e. thin layers) presents problems. The invention devices a solution to these problems by prescribing materials that can be adjusted to the correct thickness by electroplating or etching. Layers with adjustable characteristic impedance can be made as a composite of solid and polymer materials by etching grooves in the solid material, and filling the grooves with polymer, or in some situations the grooves can be unfilled. Alternatively one can grow posts or other structures of solid material by electroplating onto a substrate, the dimensions being controlled by photolithographic techniques. Using such techniques to form a casting frame for ceramics, one can also make ceramic/polymer composite films, or a ceramic post matrix where the inter-post volume is unfilled, to reduce the characteristic impedance of piezoelectric films.

By introducing more electrodes both at the front face of the transducer plate and between film layers inside the composite plate, one obtains multiple electric ports that can be efficient in different frequency bands. Electrodes at both faces of the transducer plate for example, can be used as a lower frequency electric port that is efficient around lower resonance frequencies of the plate, for example $\lambda_0/2$ resonance at $f_0=c_1/2L_x$ for the low characteristic impedance backing. According to the invention, the signals from several electric ports can be combined for improved transmit and receive characteristics, either through direct galvanic connection of electrodes, or in transmit mode through special drive signals on the electrodes, or in receive mode through a combination of the signals from electric ports after isolation amplifiers.

The structure can be laterally divided into array elements to obtain transducer arrays for electronic direction steering and focusing of the ultrasound beam.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures and procedures described herein.

DETAILED DESCRIPTION OF THE PRESENTLY PREFERRED EMBODIMENTS

Figure 1A:
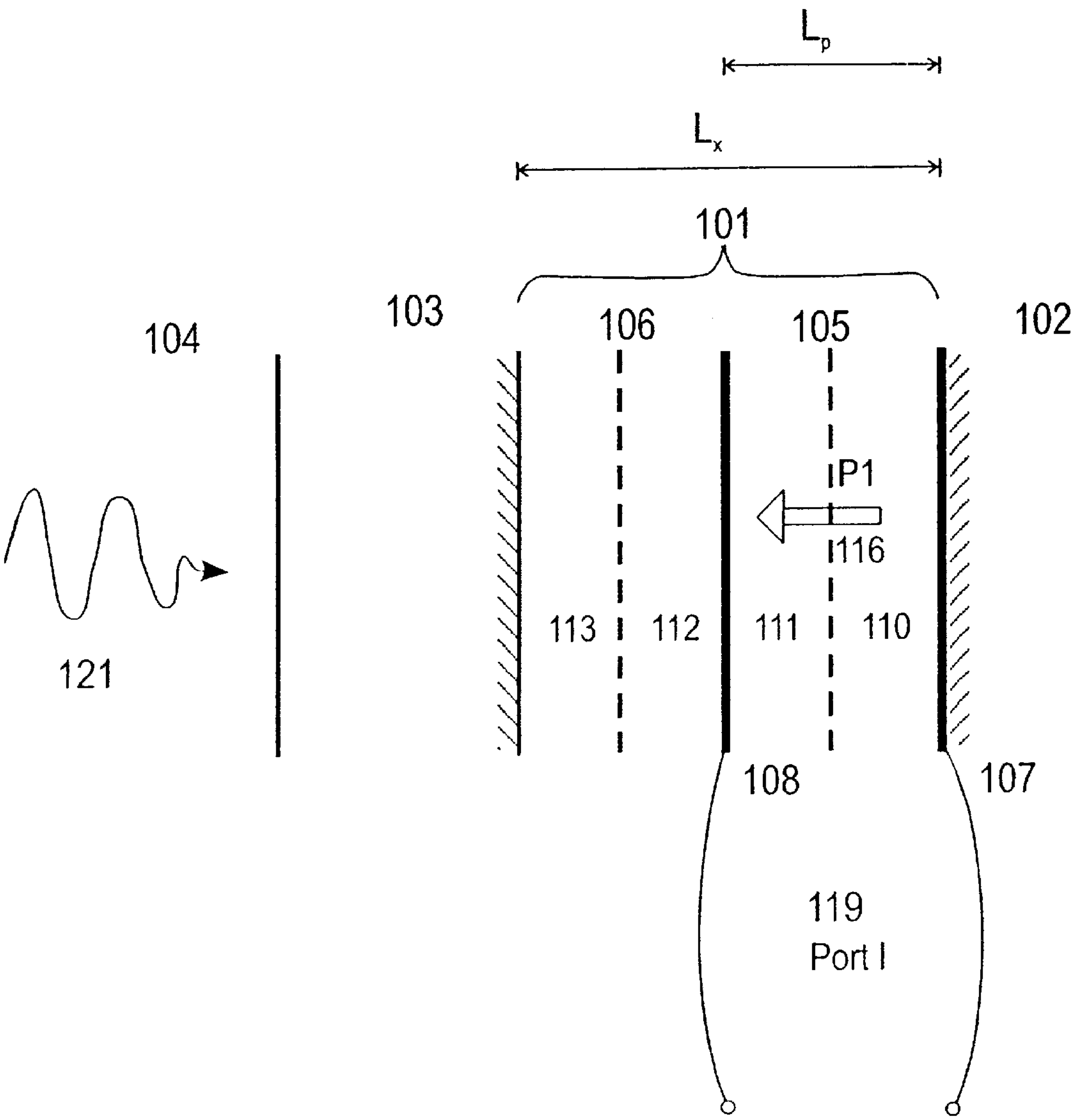
FIGS. 1*a*–1*c*, show examples of transducer structures according to the invention, where a ferroelectric ceramic plate is composed of several layers of tape cast film to provide a total plate that operates at higher order resonances in the active bands of the transducer.
Figure 1B:
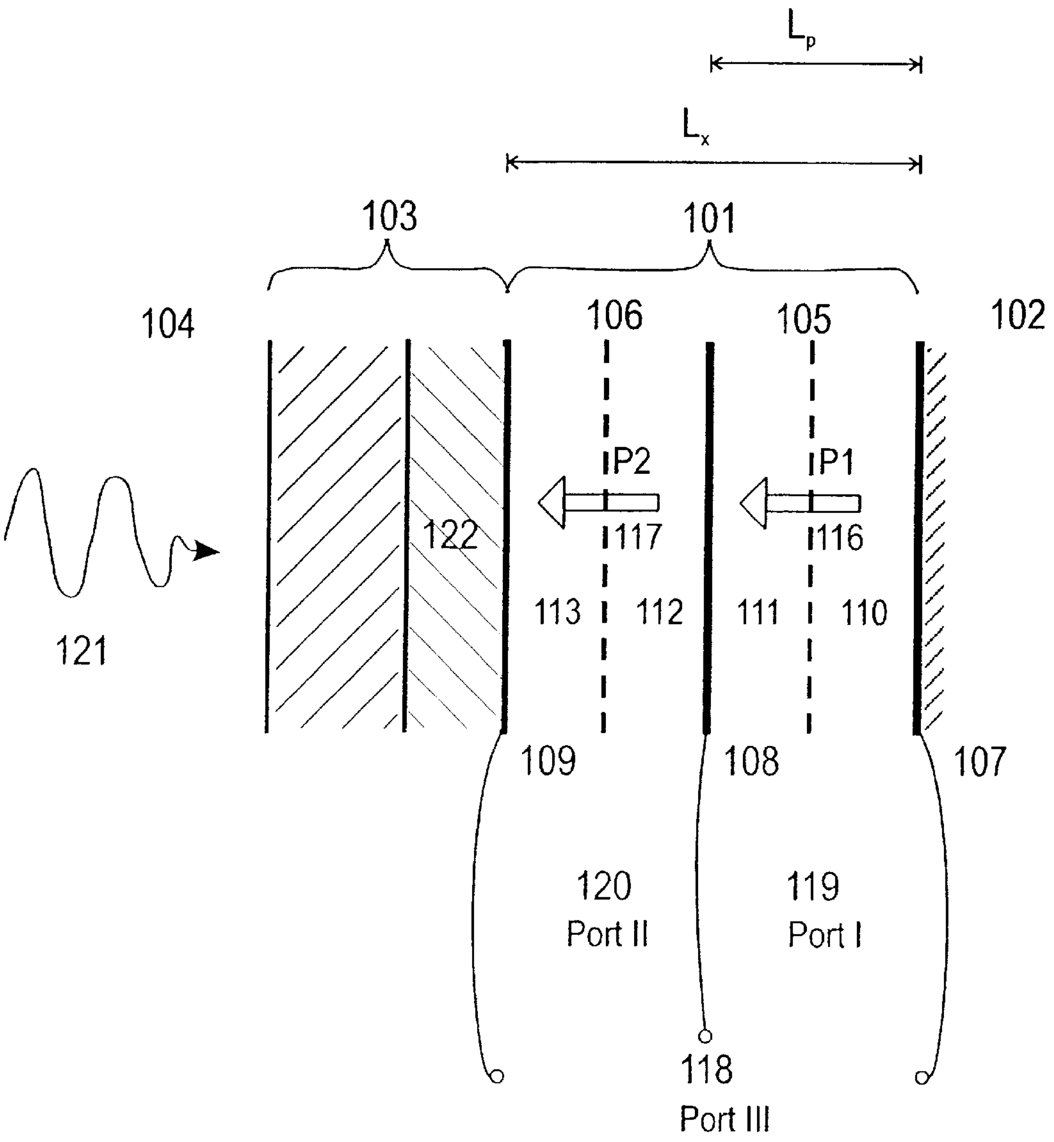
Figure 1C:
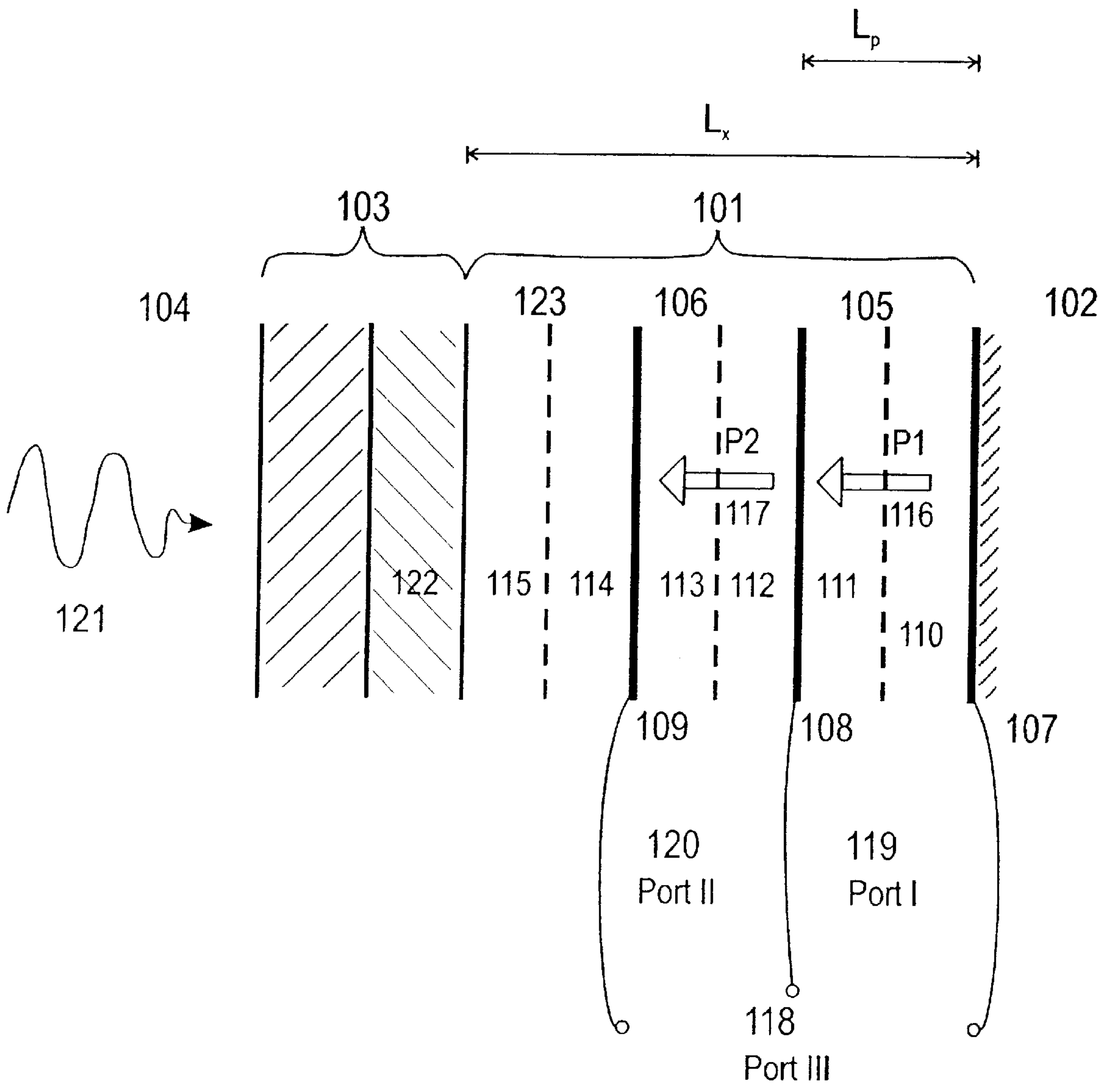

Typical embodiments according to the invention are shown in FIGS. 1*a*–1*c*, where all Figures. show a composite transducer plate 101 made of several layers of ferroelectric, ceramic films and possibly films of other material with characteristic impedance close to that of the ceramic films. In FIGS. 1*a* and 1*b* it is shown for sake of example 4 layers 110–113 of films, while in FIG. 1*c* it is shown 6 layers 110–115. The composite plate with characteristic impedance $Z_x$ is mounted on a backing material 102 with characteristics impedance $Z_B$. The backing material absorbs waves so that waves reflected from the back side of the backing can be neglected. The backing material hence appears to have infinite thickness. Back impedance matching layers can possibly be mounted between the composite ceramic plate and the backing, to improve sensitivity in selected frequency bands according to known principles. The resonant nature of such matching limits the total bandwidth, and in the following discussion the back impedance matching layers are neglected.

The front face of the composite transducer plate 101 is connected to an acoustic load material 104 (tissue or material connecting to tissue) through an acoustic load impedance matching section 103, for improved energy coupling between the vibrating piezoelectric plate and the load material. The impedance matching section is composed of one or more layers of elastic material which transforms the characteristic impedance of the tissue material (~1.5 MRayl) to a higher value, $Z_{xm}$, seen into the matching layers from the ceramic plate.

In all FIGS. 1*a*–1*c*, the 1$^{st}$ electrode 107 is mounted at the backside of the plate 101. A 2$^{nd}$ electrode 108 is mounted between layers 111 and 112. The two electrodes 107 and 108 are used to polarize the ferroelectric, ceramic material between the electrodes, where the polarization direction is by example indicated by the arrow P1, 116, in FIGS. 1*a*–*c*. This layer hence becomes piezoelectric and the two electrodes 107, 108 can be used for electromechanical coupling to constitute the electric port 119, Port I. The layer 106 in FIG. 1*a*, can be made of a conducting film with characteristic impedance close to the ferroelectric films, and hence merge as electrode material together with the electrode 108.

For minimal absorption of energy, the characteristic impedance of the backing is usually selected so that one gets a maximal reflection of ultrasound waves at the backing. This is either obtained with $Z_B \ll Z_x$ or $Z_B \gg Z_x$. The reflection at the backing produces a standing wave pattern of the thickness vibrations in the transducer plate. Best electromechanical coupling is obtained when the electrodes are placed so in this standing wave pattern that the thickness vibration amplitude of the piezoelectric material between the electrodes is maximized. The largest amplitude is found when the electrodes are placed at antinodes in the vibration pattern with opposite vibration direction, which is found when the distance between the electrodes is $L_p \sim \lambda_p/2$, where $\lambda_p$ is the wave length in the piezoelectric material at the center frequency $f_p$ of the active transduction band.

With no reflections in the backing material, the back face of the transducer plate will at all frequencies be an antinode for $Z_B<Z_x$, or a node for $Z_B>Z_x$. Antinodes of the vibration pattern in front of the backing are found at a distance $p\lambda_p/2$, p=1, 2, 3, . . . for $Z_B<Z_x$, and at $(2p-1)\lambda_p/4$, p=1, 2, 3, . . . for $Z_B>Z_x$. The antinodes in front of the backing hence moves towards the backing on hyperbolas as the frequency increases, and passes through electrodes in front of the back electrodes as the frequency increases, limiting the bandwidth of the electromechanical coupling of the electrodes. The widest bandwidth of the electrodes electromechancical coupling is then found by placing the back electrode at the back face of the transducer plate, as shown in FIGS. 1 and 2, as this is at all frequencies an antinode for $Z_B<Z_x$ and a node for $Z_B>Z_x$. The front electrode of the electric port is then placed at the first antinode in front of the backing at the center frequency of the active band, which gives a thickness of the piezoelectric layer between the electrodes of $L_p \sim \lambda_p/2$ for $Z_B<Z_x$ and $L_p \sim \lambda_p/4$ for $Z_B>Z_x$.

Maximal vibration amplitude in the transducer plate is found when the transducer plate is at a mechanical thickness resonance. The requirement for mechanical thickness resonance of the composite transducer plate, is that the sum of the round trip propagation phase in the plate and the phases of the reflection coefficients at the plate surfaces is a whole number of 2 π. The round trip propagation phase angle in the plate is $2\phi_x=\Sigma_n 2\phi_n$, where $\phi_n=k_n L_n$ is the propagation phase angle through layer #n where $L_n$ is the thickness and $k_n=\omega/c_n$ is the wave number for the thickness waves in the layer #n, and $\omega=2\pi f$ is the angular frequency of the wave. With $\lambda_n=c_n/f$ as the wave length in layer #n, this implies that mechanical resonances are found for $Z_B<Z_x$ when $\Sigma_n L_n/\lambda_n \sim p/2$, p=1, 2, 3, . . . For $Z_B>Z_x$ we obtain mechanical resonances when $\Sigma_n L_n/\lambda_n \sim (2p-1)/4$, p=1, 2, 3 , . . .

By way of example, FIGS. 1*a*–1*c* shows that each layer is composed of two films of equal thickness and same type of ceramic material. This gives a thickness of the port layer of $L_p \sim \lambda_p/2$ when the thickness of the composite plate is $L_x \sim \lambda_p$ in FIGS. 1*a* and 1*b*, and $L_x \sim 3\lambda_p/2$ in FIG. 1*c*. The maximal electromechanical coupling of the electrodes is hence found at the mechanical thickness resonances of the plate, maximizing the sensitivity of the transducer plate around the resonance frequencies. The resonance of the piezoelectric plates are modified when current flows in the electrodes, and the thickness of the layers must be tuned around these values for best performance.

To increase the bandwidth of this resonance, and hence also the bandwidth of the active transduction band of the transducer, one uses a load impedance matching that is efficient in a wide band around the center frequency $f_p$. Adequate designs are for example found with λ/4 thickness of the matching layers at $f_p$ and characteristic impedance of the layers determined for example from an equal ripple or maximally flat requirement on the reflection coefficient $R_{xm}$ seen from the ceramic plate into the load matching section.

With equal ripple of $R_{xm}$ in the pass band, the characteristic impedances $Z_n$ of the matching layers are symmetric in the following respect $$Z_n = \frac{Z_{rxm} Z_L}{Z_{N+1-n}} \quad (1)$$
$$n = 1, 2, \ldots, N$$

where n labels the matching layer number from the load material towards the ceramic layer, and N is the total number of matching layers. $Z_{rxm}$ is a reference impedance seen into the matching layers into the load. For two matching layers, one can choose $Z_1$, defining the ripple-level of the reflection coefficient $R_{xm}$, and Eq.(1) then gives the impedance of the other layer as $Z_2=Z_{rxm}Z_L/Z_1$. For an odd number of layers N, we get from Eq.(1) for the mid layer n=k=(N+1)/2 that $Z_k=\{Z_{rxm}Z_L\}^{1/2}$. With a 3-layer matching $Z_2=\{Z_{rxm}Z_L\}^{1/2}$ is given, and selecting $Z_1$ defines the ripple level of $R_{xm}$, while Eq.(1) gives $Z_3=Z_{rxm}Z_L/Z_1$.

For a maximally flat variation of $R_{xm}$ in the pass band, the characteristic impedances $Z_n$ of the matching layers can be calculated from the formula $$\ln\frac{Z_{n+1}}{Z_n} = \frac{C_n^N}{2^N}\ln\frac{Z_L}{Z_{rxm}} \quad (2)$$
$$C_n^N = \frac{N!}{(N-n)!n!}$$
$$n = 1, 2, \ldots, N$$

Figure 2A:
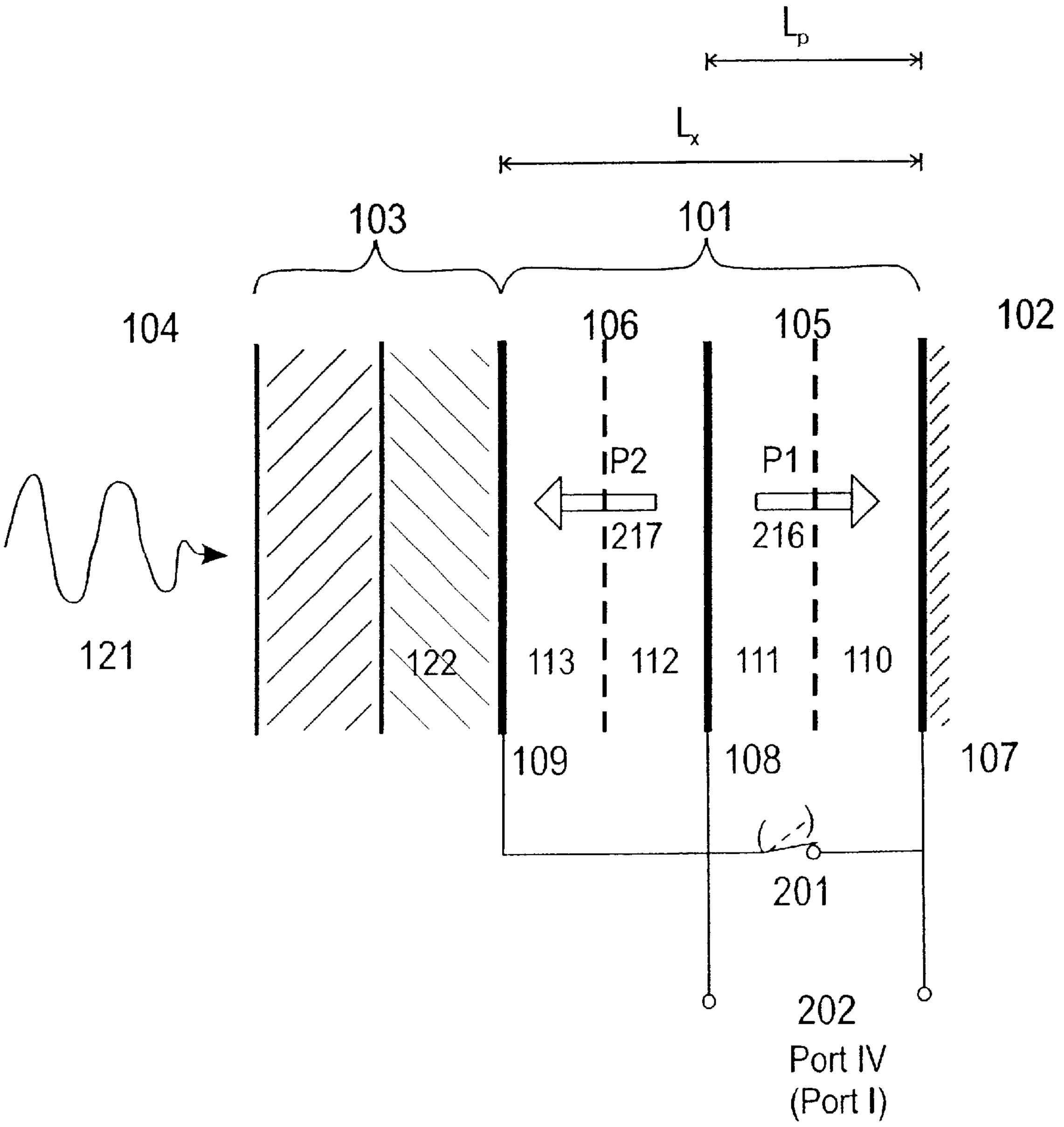
FIGS. 2*a* and 2*b*, show other examples of transducer structures according to the invention, where a ferroelectric ceramic plate is composed of several layers of tape cast film to provide a total plate that operates at higher order resonances in the active bands of the transducer.
Figure 2B:
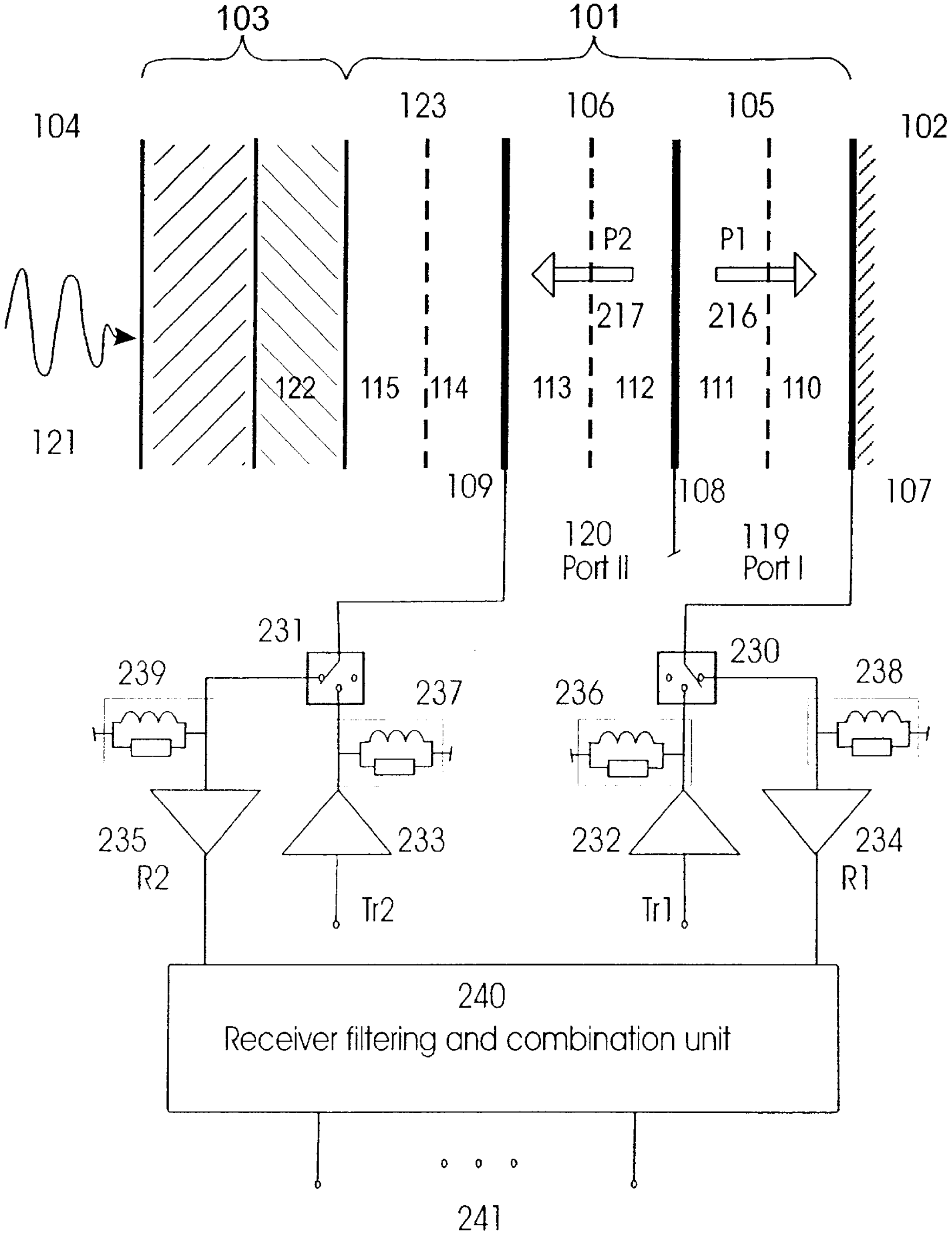
Figure 3A:
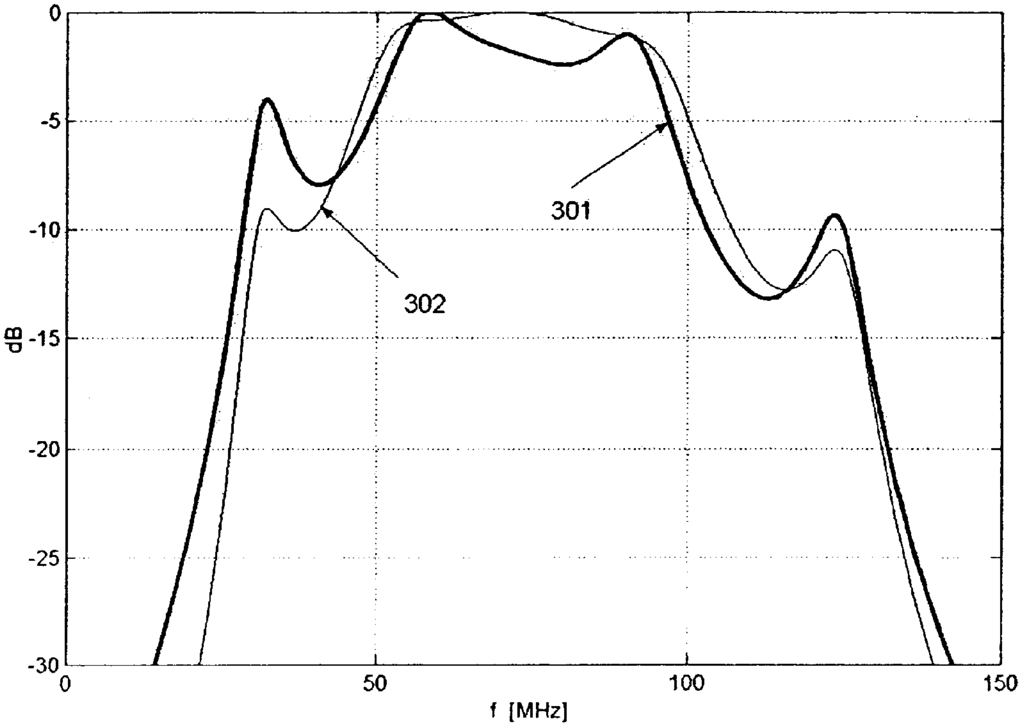
FIGS. 3*a*–3*c*, show examples of transmit and receive transfer functions for transducer structures in FIGS. 1*a*, 1*b*, and 2*a* with a 2-layer load matching where one matching layer is made of aluminum.

An example transmit transfer function, $H_{tt}(\omega)$, from the drive voltage of Port I (119) (defined in FIGS. 1, 2) to the vibration velocity of the matching layer load face is shown as 301 in FIG. 3*a*. A 2-layer matching is used with $\lambda_m/4$ thickness at 75 MHz and characteristic impedance $Z_1$=3.3 MRayl and $Z_2$=17 MRayl. In receive mode we assume an incident pressure wave indicated as 121 in FIGS. 1*a–c* and FIGS. 2*a,b*. The wavefronts of 121 is assumed to be conformal with the transducer surface. The receive transfer function, $H_{rt}(\omega)$, from the pressure amplitude of the incident wave to the voltage across a tuned receiver network is shown as 302 in FIG. 3*a*.

We note that the port has an active band both in transmit and receive modes from 50 to 100 MHz, which gives a relative bandwidth of 67%. With $c_1$=4380 m/s we get a total plate thickness $L_x$=54 μm for a short circuit $\lambda_p/2$ resonance of the electric port of $f_0$=75 MHz. The λ/2 short circuit resonance of the whole ceramic plate corresponds to $f_{\lambda/2}$~40 MHz. This design hence allows for a center frequency of the active transducer band that is around twice $f_{\lambda/2}$.

A characteristic impedance of $Z_1$~3.3MRayl can be obtained with some polymer materials, which for example can be sputtered or spin coated to the right thickness on the transducer structure. A characteristic impedance of $Z_2$~17MRayl is found for aluminum (Al), which is hence conveniently used as the matching layer closest to the plate. Al for this matching layer has several advantages: 1) The layer can be rolled, etched, or grown electrolytically to the right thickness with good thickness control. 2) As Al is electrically conducting, it can be grounded to serve as a shield for the inner electrodes against interference from external electromagnetic sources, or it can be used as an active electrode as shown in FIG. 1*b*. In this Figure. the Al layer is indicated as 122 and is electrically connected and merging with the electrode 109 on the front side of the ceramic layer 106. Electrodes 109/122 and 108 can then be used to polarize the ceramic layer 106 between the electrodes, where the direction of polarization is by example indicated by the arrow P2, 117, in FIGS. 1*b* and 1*c*. The layer 106 hence becomes piezoelectric and can be used for electromechanical coupling, constituting with electrodes 109 and 108 an electric port, Port II, shown as 120 in FIGS. 1*b* and 1*c*. Another interesting material for matching layer is silicon (Si) which has a characteristic impedance ~19 MRayl, and hence has close to the same acoustic effect as Al. Si can also function as an electrode, especially with heavy doping.

Figure 5A:
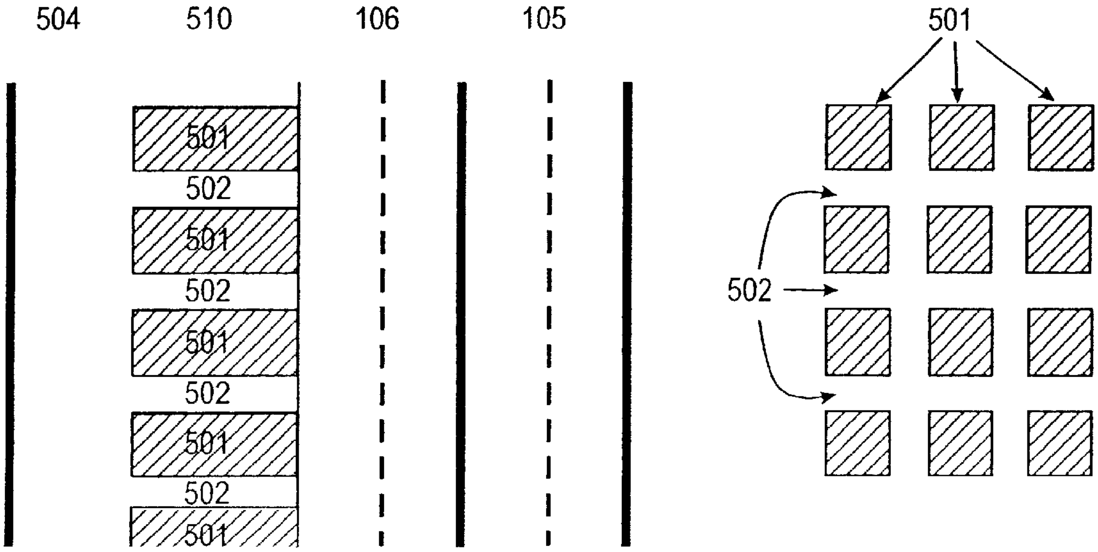
FIGS. 5*a*–5*c*, show examples of solid/polymer composites used as acoustic impedance matching layers.

Lower characteristic impedance matching layers can be formed as composites of polymer and a solid material. Such composites can for example be made by etching grooves in a solid layer, and filling the grooves with a softer polymer to form the solid/polymer composite. This is illustrated in FIG. 5*a*, where 510 shows the 2nd matching layer made as a solid/polymer composite with characteristic impedance $Z_2$, deposited on the ceramic layer 106. Starting with a complete solid layer, the grooves 502 are etched in a pattern defined with standard photo lithographic techniques that leaves the solid posts 501. The grooves are then filled with polymer material to form the solid/polymer composite together with the remaining solid posts 501. The polymer can in many situations be the same as the material of the 1st matching layer 504 with characteristic impedance $Z_1$, so that filling of the grooves and deposition of the $1^{st}$ matching layer is done in the same operation, for example through sputtering or spin coating techniques. The relative volume of the solid posts 501 and the polymer 502 is tuned so that characteristic impedance of the $2^{nd}$ layer of $Z_2$ is obtained.

Note that such a solid/polymer composite technique opens for the use of a wide variety of materials for matching layers, such as magnesium (Mg: $Z_0$~10 MRayl), glass (glass: $Z_0$~13 MRayl) gallium arsenide (GaAs: $Z_0$~26 MRayl), germanium (Ge: $Z_0$~27 MRayl), titanium (Ti: $Z_0$~27 MRayl), Zinc (Zn: $Z_0$~30 MRayl), zirconium (Zr: $Z_0$~30 MRayl), silver (Ag: $Z_0$~38 MRayl), copper (Cu: $Z_0$~44 MRayl), gold (Au: $Z_0$~62 MRayl), palladium (Pd: $Z_0$~68 MRayl), or platinum (Pt: $Z_0$~85 MRayl), or mixtures of the above.

Figure 5B:
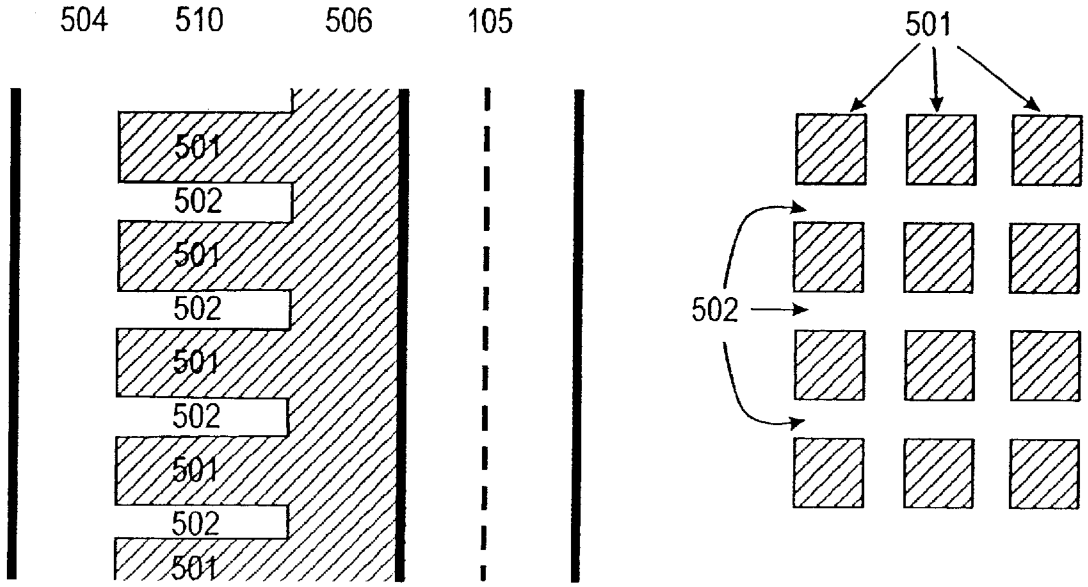

One should also note that Zn, Zr, and Ag has characteristic impedances close to the ceramic material (ferroelectric ceramic: $Z_0$~34 MRayl). With a layer of such a material attached to a ceramic layer, the thickness vibration resonance frequencies are defined by the total thickness L, of the ceramic and metal layers, through the round trip propagation phase, $\Sigma_n 2\phi_n$, and the phases of the reflection coefficients at the surfaces of the structure, as described above. The transfer functions in FIG. 3*a* will then only be slightly changed, if layer 106 in FIG. 1*a* is substituted with one of these materials, illustrated as 506 in FIG. 5*b*, mounted on a ceramic layer 105. Etching grooves 502 in the surface of these materials leaves the solid posts 501. The grooves are then filled with polymer to form the $2^{nd}$ load impedance matching layer 510 of solid/polymer composite. As above, the $1^{st}$ matching layer 504 can be deposited together with the filling of the grooves.

The solid posts of the composite could also be grown by electroplating the posts onto a metal layer instead of etching the grooves into the layer. The metal layer is then first covered with photo resist polymer, that is removed with standard photo lithographic techniques at the locations where the solid posts are to be grown. For thin composite layers, the remaining layer of photo-resist polymer could then be used as the polymer fill.

To avoid lateral modes, the lateral dimensions of both the solid posts 501 and the grooves 502 should be less than half a wave length for the slowest waves in the materials, which are the shear waves. With a shear wave velocity of 1000 μm/μs in the polymer one gets maximal thicknesses at 100

MHz of 5 μm for the polymer grooves. Similarly one should make sure that the width of the solid posts is less than half of the wavelength of shear waves in the solid. This gives a lower limit on the thickness of the solid posts that is ~3–5 times the width of the polymer grooves. Lateral modes can also be inhibited by using irregular spacing of the grooves.

Driving a voltage between electrodes 107 and 109 of FIGS. 1*b* and 1*c*, we get a third electric port, Port III, shown as 118 in FIGS. 1*b* and 1*c*. This port can be considered as a series coupling of Port I and Port II, where the currents in the ports are the same, while the voltages of Port I and Port II are added to give the voltage of Port III. A parallel coupling of Port I and Port II can be obtained as in FIG. 2*a*, where the polarization of the layers 105 and 106, indicated by P1 (216) and P2 (217), have opposite directions to each other. The parallel coupling, where the voltages across Port I and Port II are the same while the currents are added, is then obtained by direct electrical connection between electrodes 107 and 109, for example by the switch 201, and coupling the voltage between these electrodes and the center electrode. Opening the switch 201 then turns the port at 202 into Port I of FIG. 1*b*.

Figure 3B:
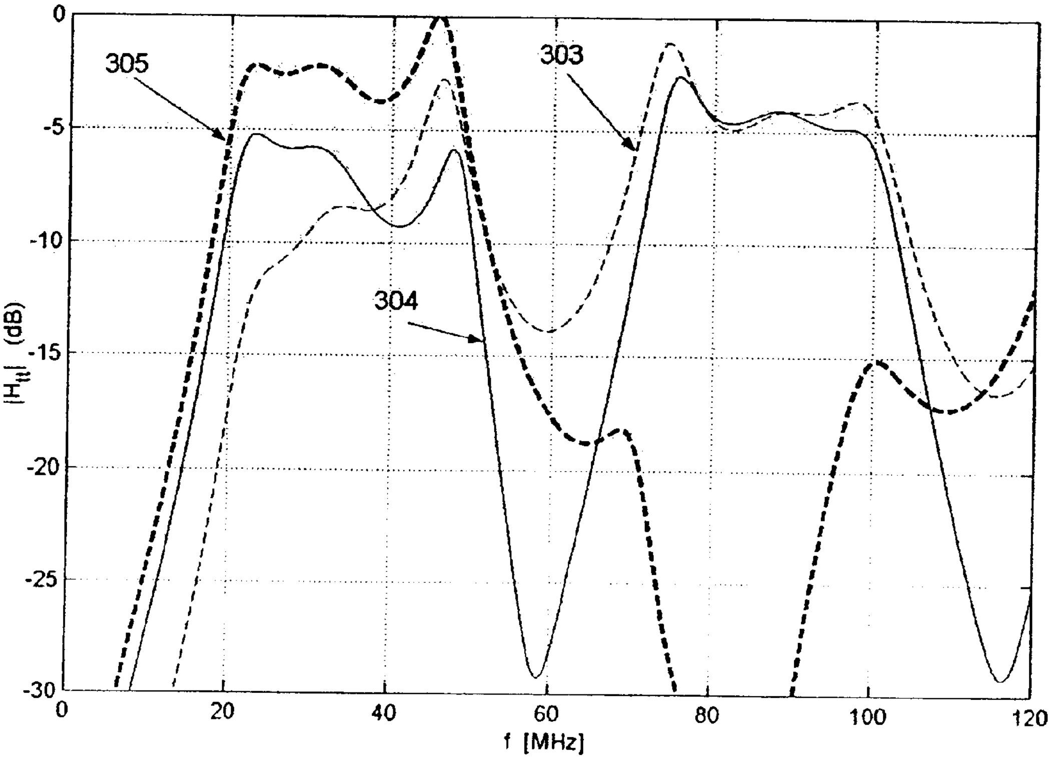

Example transmit transfer functions, $H_{tt}(\omega)$, from drive voltage to front face vibration velocity are shown in FIG. 3*b* for Port I (303), Port II (304), and Port IV (305) of FIGS. 1*b* and 2*a*. A 2-layer load matching is used where the inner matching layer is aluminum with characteristic impedance $Z_2$=17 MRayl and the outer matching layer has characteristic impedance $Z_1$=3.5 MRayl. The thickness of the matching layers are chosen to $\lambda_m/4$ at 30 MHz, which gives $3\lambda_m/4$ at 90 MHz. The thickness of the piezoelectric layers are chosen to $\lambda_m/4$ short circuit resonance at ~39 MHz, i.e. $\lambda_p/2$ short circuit resonance at ~80 MHz. The thickness of the total ceramic plate is hence $\lambda_p/2$ short circuit resonance at ~39 MHz, i.e. $\lambda_p$ short circuit resonance at ~80 MHz, consistent with the introduction in Section 3.

We note that Port IV (305) gives a low frequency transmit band in the 20–50 MHz range, similar to Port II (304) while Port II (304) in addition gives a high frequency transmit band in the 70–100 MHz range, where Port IV gives very low values of the transfer function. Port I (303) gives a flat high frequency transmit band in the 70–100 MHz range, while the low frequency range shows an inadequate variation of the transfer function. Port II hence gives nice transmit in both the low and the high frequency bands, while the transmit transfer function of Port IV (305) shows high attenuation in the high frequency band.

Figure 3C:
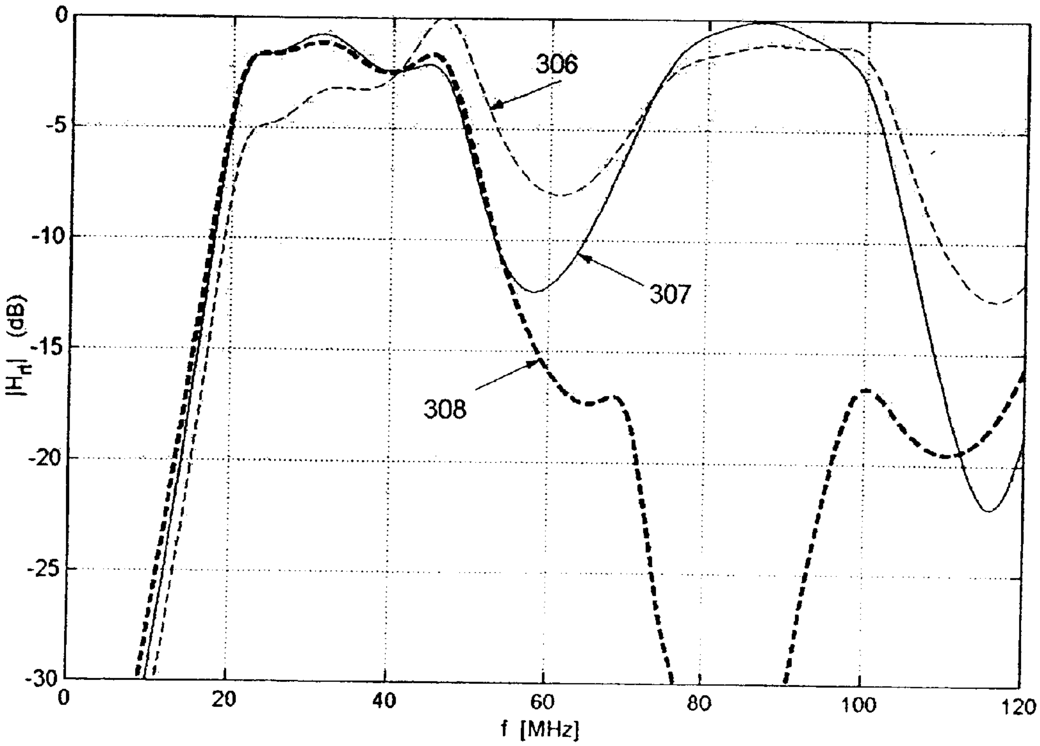

Example receive transfer functions, $H_{rt}(\omega)$, from the pressure amplitude in the incident wave 121 to received voltage across a tuned impedance, are shown in FIG. 3*c* for Port I (306), Port II (307), and Port IV (308) for same structure as in FIG. 3*b*. We note that the transfer function of Port IV (308) shows a low frequency receive band in the 20–50 MHz range, while both Port I (306) and Port II (307) shows both a low frequency (20–50 MHz) and a high frequency (70–100 MHz) receive band.

The combined results of FIGS. 3*b* and 3*c* show that this transducer structure is well suited for $1^{st}$ harmonic imaging in both a low (20–50 MHz) and a high frequency (70–100 MHz) band, $2^{nd}$ harmonic imaging with transmit center frequency ~40 MHz and receive center frequency ~80 MHz, $3^{rd}$ harmonic imaging with transmit center frequency 30 MHz and receive center frequency ~90 MHz, and sub harmonic imaging with a transmit center frequency ~80 MHz, and a receive center frequency ~40 MHz. Especially we note that the low values of the Port IV transmit transfer function around 80 MHz, makes this port well suited for transmitting pulses ~40 MHz for $2^{nd}$ harmonic imaging.

One can further increase the thickness of the composite ceramic plate by added film layers 114–115 composing the layer 123 as shown in FIG. 1*c*, with two active piezoelectric layers 105 and 106. The layer increases the effective bandwidth of the structure by lowering the fundamental resonance of the plate, and the increased thickness improves the stability of the plate in the sintering process and during other handling of the plate. With deposition of the films onto a substrate, the layer 123 can be used as contamination isolation between the substrate and the functional ceramic layers 105 and 106, as described below.

Figure 4A:
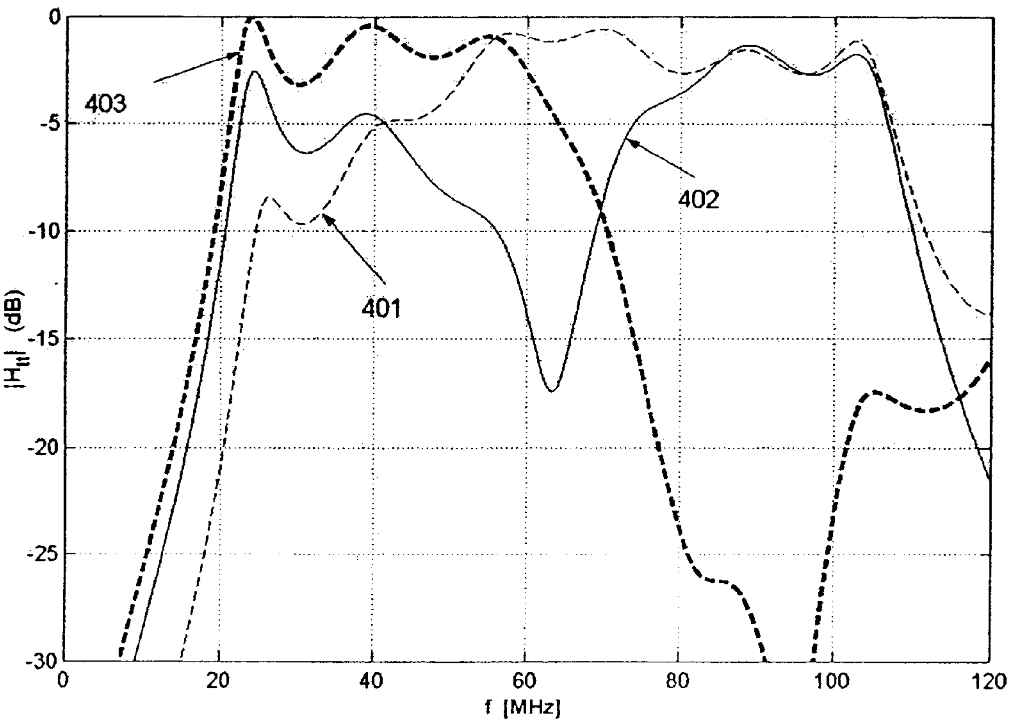
FIGS. 4*a*–4*c*, show examples of transmit and receive transfer functions for transducer structures in FIGS. 1*c* and 2*b* with a 3-layer load matching where one of the layers is made of aluminum.

Examples of transmit transfer functions, $H_{tt}(\omega)$, of the transducer in FIG. 1*c* with 3 load matching layers are shown in FIG. 4*a* for Port I (401), Port II (402), and Port IV (403). The characteristic impedances of the matching layers are $Z_1$=2.9 MRayl, $Z_2$7 MRayl, and $Z_3$=17 MRayl. In the example, the matching layers have $\lambda_m/4$ thickness at 65 MHz, the piezoelectric layers have $\lambda_p/4$ short circuit resonance at 42 MHz, and the front ceramic layer 123 have $\lambda_p/4$ open circuit resonance at 54 MHz.

Due to the lower thickness of the load matching layers in FIG. 4*a*, the transfer function of Port I (401) is missing the dip around 60 MHz found in FIG. 3*b*, and can hence be used to transmit frequency components also around 60 MHz. The transfer function of Port II (402) has a dip around 60 MHz produced by its location in the standing wave pattern of the piezoelectric layers. The transfer function of Port IV (403) shows a wider transmit band (20–65 MHz) compared to FIG. 3*b*.

Figure 4B:
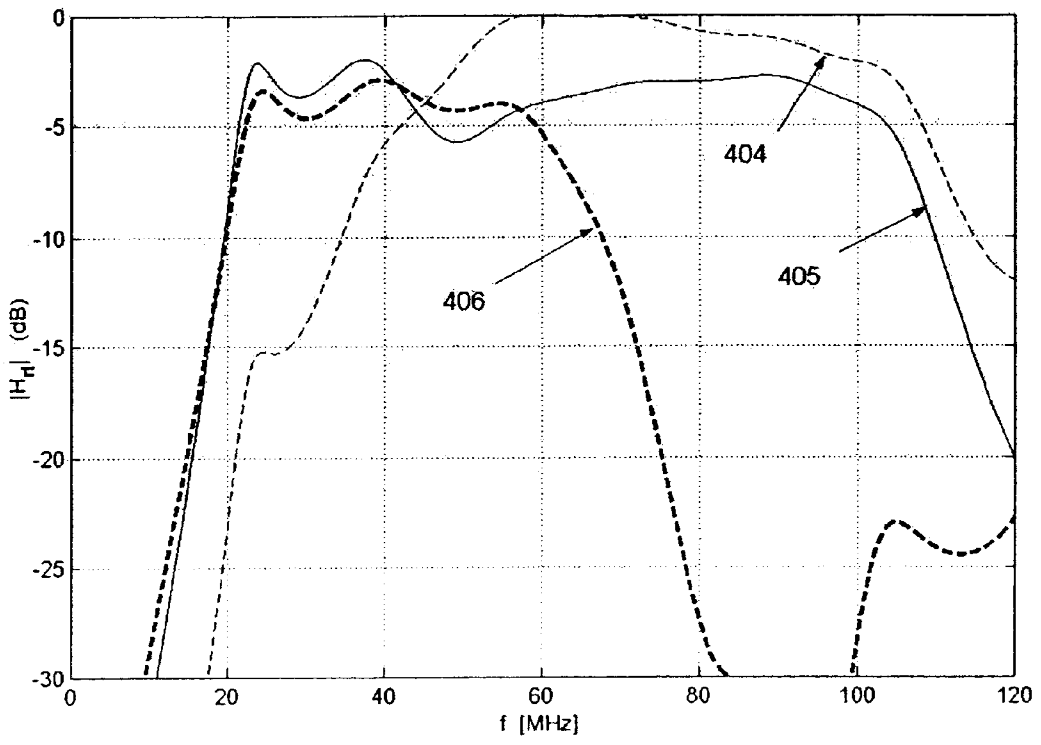

Receive transfer functions, $H_{rt}(\omega)$, from the pressure amplitude in the incident wave to received voltage across a tuned impedance, are shown in FIG. 4*b* for Port I (404), Port II (405), and Port IV (406) for the same structure as in FIG. 4*a*. We note the transfer function of Port IV (406) shows a low frequency receive band in the 20–60 MHz range, while Port II (405) shows efficient reception in a wide band from 20–100 MHz. Port I (404) shows somewhat better sensitivity than Port II in a slightly narrower band from 40–105 MHz.

One should note that a series coupling of Port I and Port II to Port III for the transducers discussed above gives similar transfer functions as Port IV, with higher electric input impedances.

The displays in FIGS. 4*a* and 4*b* show that the transducer structure in FIG. 1*c* provides wider bandwidths of the ports than the structure in FIG. 1*b*. The total thickness of the ceramic plates for the examples of FIGS. 4*a* and 4*b* is 66 μm, which is higher than for the structure related to FIGS. 3*a–c*. This provides higher stability of the ceramic plate during sintering and other handling, with still higher upper frequencies of the efficient transduction band. Per the discussion above, we note that the outer layer 123 of FIGS. 1*c* and 2*b* could be made of Zn, Zr, or Ag, or even solid/polymer composites with the solid materials of higher characteristic impedances , like copper (Cu), gold (Au), or platinum (Pt).

Figure 5C:
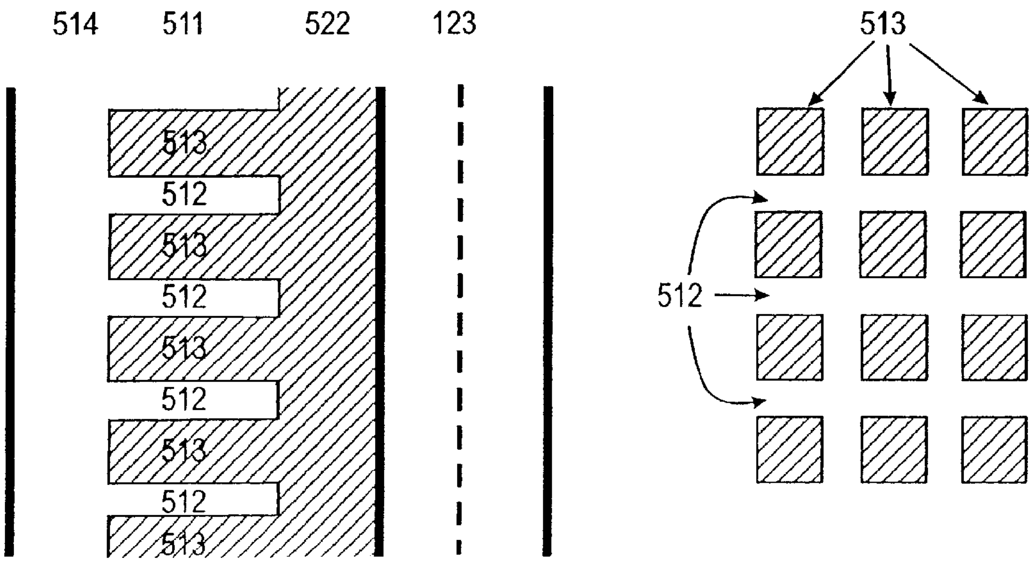

The last matching layer close to the ceramic in the example above, can be aluminum ($Z_3$~17 MRayl) or Si ($Z_3$~19.6 MRayl) that can be rolled, grinded, etched, grown electrolytically, etc., to the correct thickness. The second matching layer can be made as an Al/polymer or Si/polymer composite, for example obtained by etching grooves in the solid and filling the grooves with polymer as illustrated in FIG. 5*c*. Here 522 shows the base solid layer with the characteristic impedance $Z_3$~17 or 19.6 MRayl, deposited on the layer 123 by example. The composite solid/polymer layer used as the $2^{nd}$ matching layer is shown as 511 with the polymer grooves 512 and solid posts 513, and 514 shows the $1^{st}$, outer matching layer, which is conveniently made of a polymer with characteristic impedance $Z_1$~2.9 MRayl. The characteristic impedance of the composite solid/polymer layer 511 is tuned to the desired value $Z_2$~7 MRayl by the relative volume fill of solid/polymer. The outer polymer layer 514 can then for example be adhered together with the filling of the grooves 512 with polymer, for example by spin coating or sputtering techniques. Instead of etching, the aluminum posts 513 can be grown electolytically onto the aluminum layer, defining the growing areas and the cross sections of the post through photo-lithographic techniques, as described above As described above, silicon has close to the same characteristic impedance as aluminum (Al: $Z_0$~17.3 MRayl, Si: $Z_0$~19.6 MRayl), and is therefore also conveniently used as the load matching layer closest to the ceramic plate, where adequate thickness of the Si layer for example can be obtained through etching. The thickness of layer #3 (522) and #2 (511) is then etched first, followed by etching of the grooves 512 in the silicon, defined through photo lithographic techniques. The depth of the grooves defines the thickness of layer #2. Tapering of the width of the grooves 512 with depth can be used to obtain a layer 511 with tapered impedance, to improve the bandwidth of the matching according to known methods. Si can also be used as an electrode, especially with heavy doping.

With deposition of ceramic film onto a substrate, the sintering of the ceramic layer at high temperatures ~1000° C. can introduce problems with contamination from the substrate into the near ceramic, destroying the ferroelectric and hence piezoelectric properties of the contaminated ceramic. The structures in FIGS. 1*a*, 1*c*, 2*b* are then specially interesting for deposition of the ceramic films onto a contaminating substrate, where the front ceramic layer, 106 in FIG. 1*a*, and 123 in FIGS. 1*c*, 2*b* functions as isolation to avoid destruction of the active piezoelectric layers, 105 in FIGS. 1*c* and 2*b*. After the sintering and other mounting and processing of the transducer, the Si substrate can be etched to correct thickness, at least in front of the transducer. One then does a combined etching of the thickness of the $3^{rd}$ and the $2^{nd}$ layer before the etching of the grooves in the $2^{nd}$ layer using photo lithographic techniques to cover the areas that should not be etched.

With deposition of the ceramic onto a substrate or also when using sol gel techniques, the invention devices a method to make accurate cuts in the ceramic film, by etching a casting frame pattern in a substrate before the deposition of ceramic, as illustrated FIG. 6. FIG. 6*a* shows to the left a cross section of the substrate 601, where a pattern has been etched in the right surface leaving the walls 602 of the casting frame. The casting frame dents are filled with ceramic film 603. The casting frame walls 602 are then removed by etching, leaving independent islands of ceramic film 603 separated by the cuts 604 as shown in FIG. 6*b*. With sufficiently conducting substrate, the substrate can be used as a ground electrode, and adhering electrode material 605 on the top of these islands 603 of ceramic film, one can use the ceramic islands as elements in a transducer array.

Figure 6A:
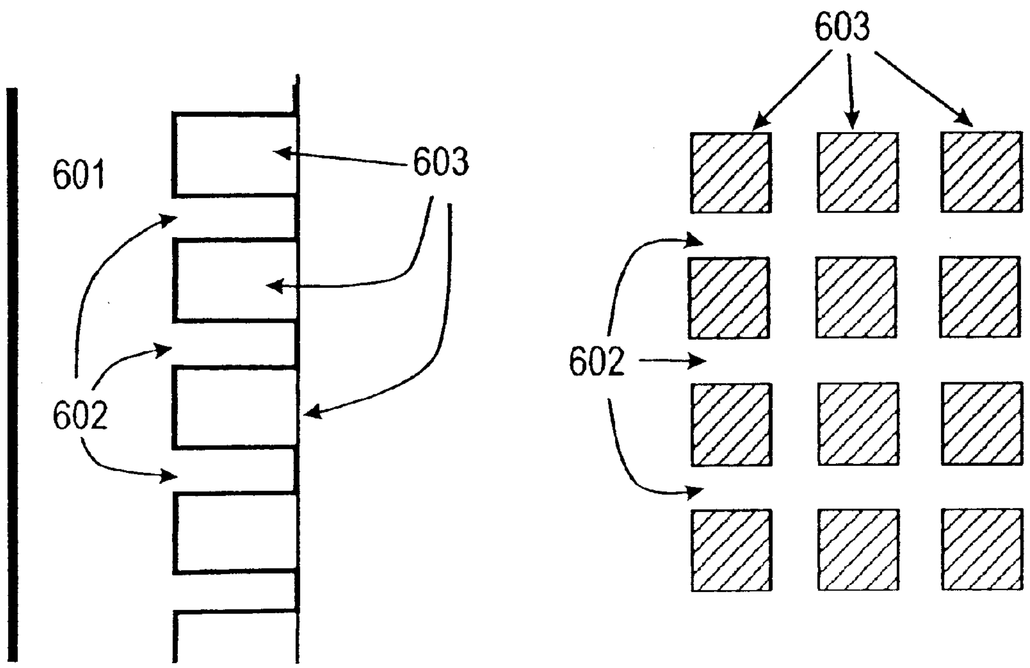
FIGS. 6*a*–6*d*, show examples of manufacturing of transducer array elements and ceramic piezoelectric composites.
Figure 6B:
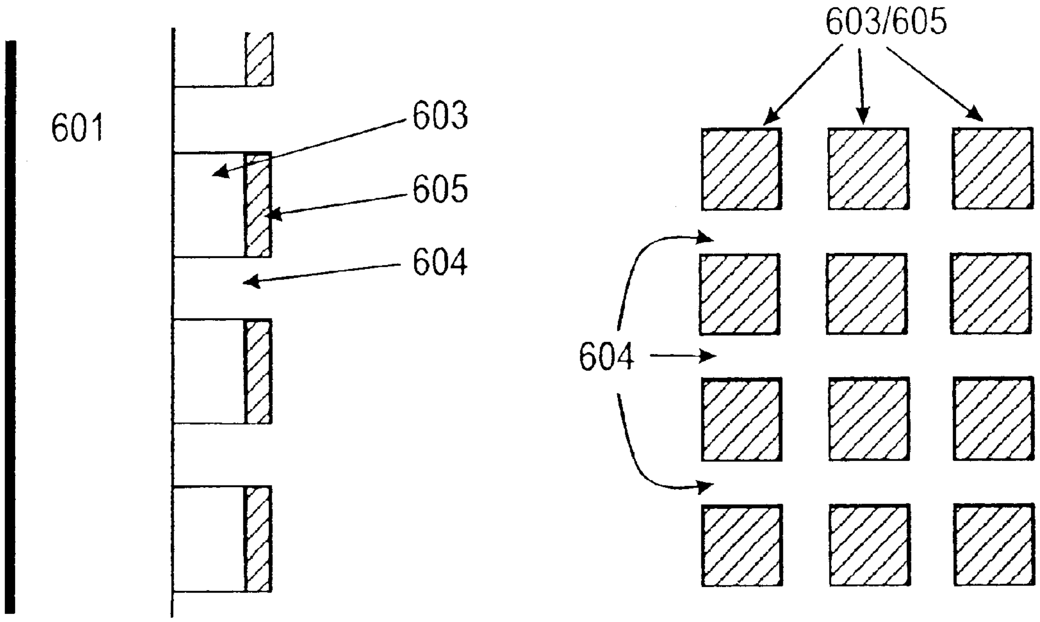
Figure 6C:
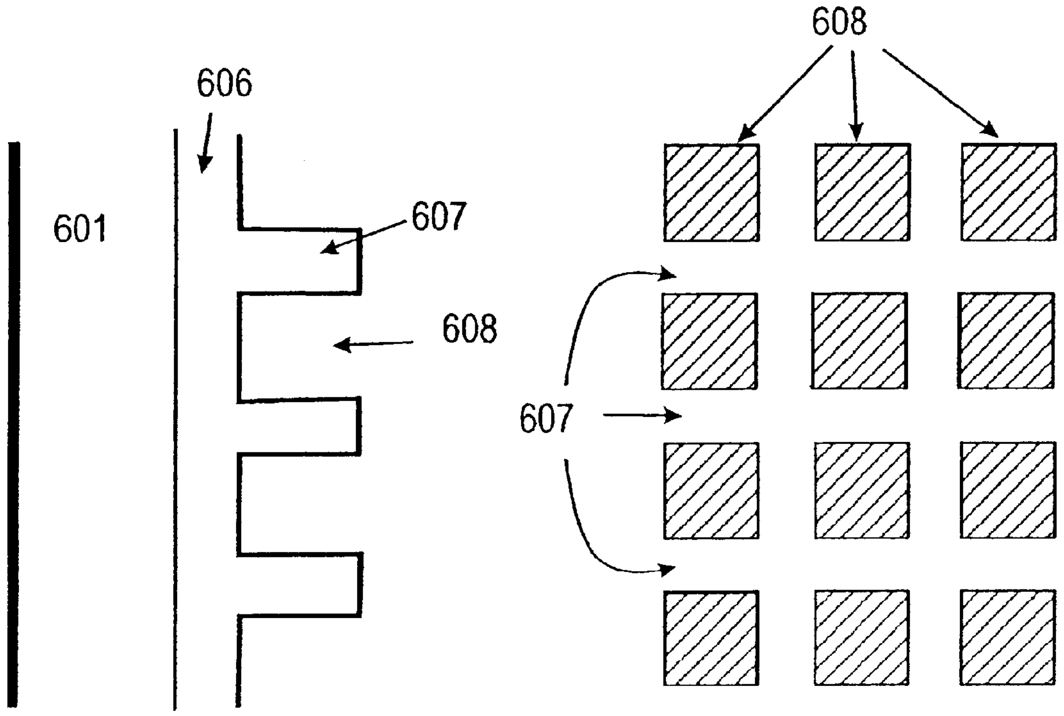

When the substrate is not sufficiently conducting to form the bottom electrode, one can first add conducting electrode material onto the substrate and etch a casting frame in the bottom electrode as illustrated in FIG. 6*c*, where 606 shows a cross section of a metal electrode on the substrate 601. The casting frame can be obtained by chemical or laser etching the dents 608 into the electrode, leaving the walls 607, for example defined through photo-lithographic techniques. The casting frame can also be made by electroplating the frame walls 607 onto the electrode, defining the pattern by photolithographic techniques, or other convenient techniques.

Figure 6D:
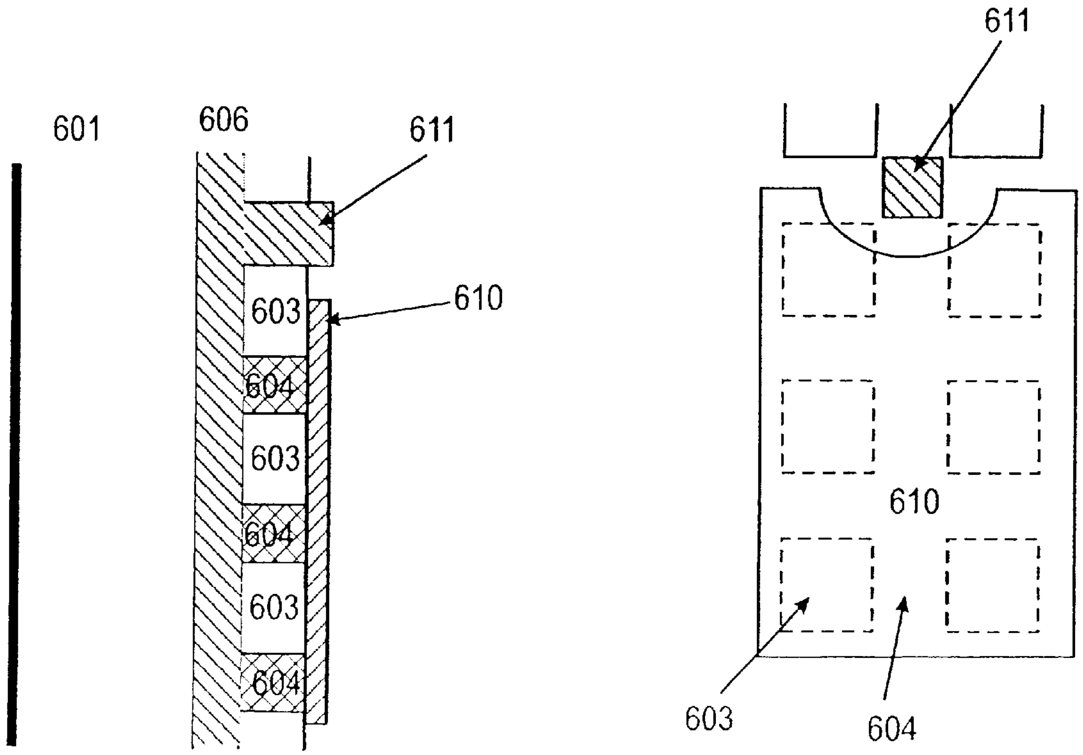

Filling the dents 608 in the casting frame with ceramic material, followed by etching of the walls 607, and filling after the sintering of the ceramic the dents between the ceramic islands with material with lower characteristic impedance, for example a polymer, one can obtain a composite as illustrated in FIG. 6*d*, with reduced average characteristic impedance. Here 603 shows the ceramic elements while 604 shows the low impedance material, which also could be no material. Larger array elements can then be defined by connecting several ceramic islands with a common electrode 610. Contact to the bottom electrode can then for example be obtained via the post 611 that is obtained by inhibiting etching in a region, for example defined by photo-lithographic techniques. When the bottom electrode is a common ground, it can also be connected by the side of the whole array.

With ~50% volume fill of ceramic in the composite, the average characteristic impedance of the composite can be made close to that of silicon (or also aluminum). An Si substrate then can function as the added elastic layer 106 in FIG. 1*a* and 123 in FIGS. 1*c* and 2*b*. The load matching layer closest to the added elastic layer can then be made as a composite of silicon and polymer, as described in relation to FIG. 5.

Figure 7:
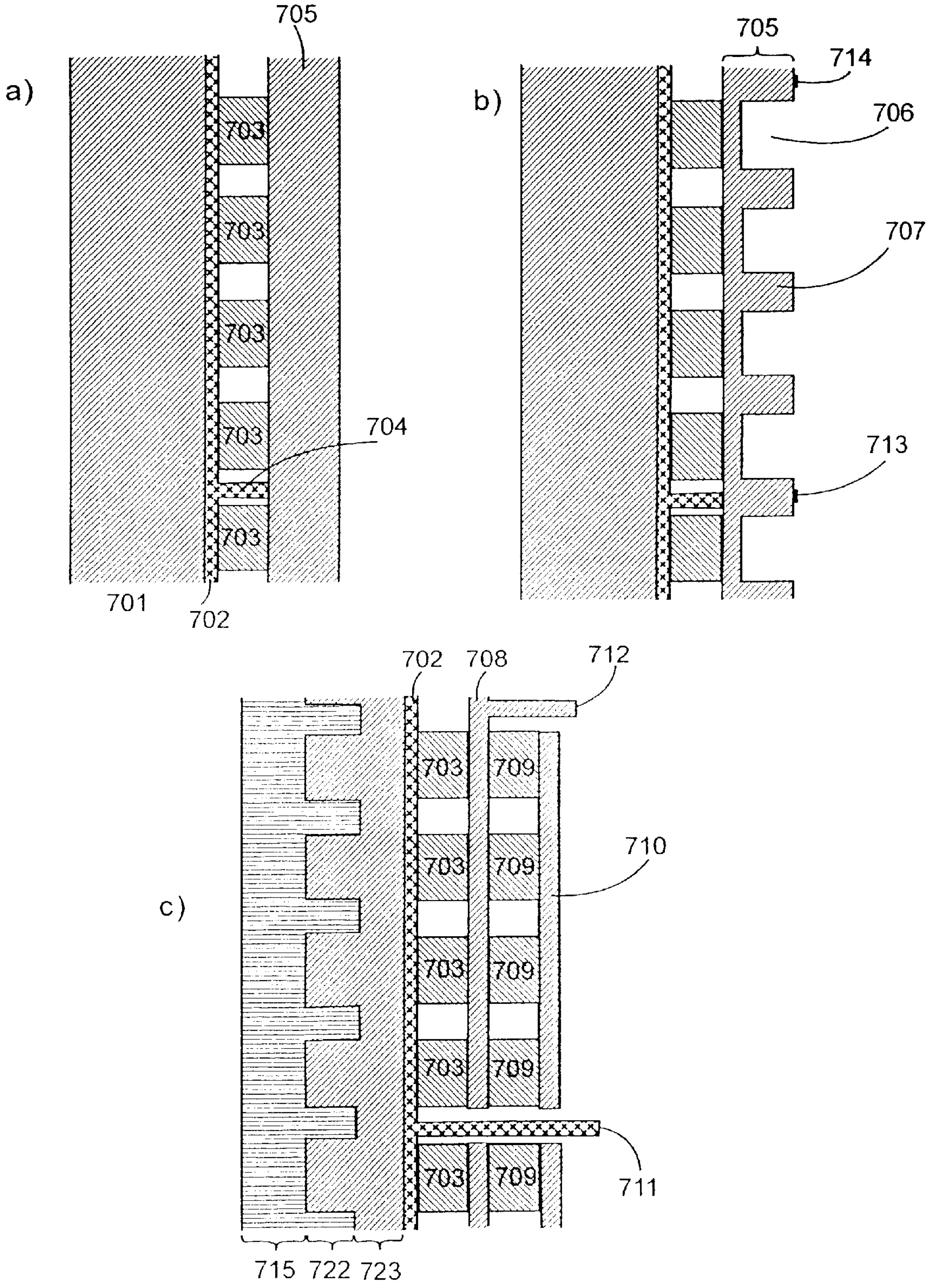
FIGS. 7*a*–7*c*, show examples of manufacturing of multiple layers of ceramic piezoelectric composites for multiple electric ports.

For multiple layer electric ports with composite ceramic material, one needs continuous electrodes between the ferroelectric ceramic layers, and hence one must avoid that the intermediate electrode layers are etched fully through when etching away the walls of the casting frame. A method where this is obtained, is shown in FIG. 7. In FIG. 7*a*, 701 shows a substrate with an electrode 702 that is etched into a casting frame as described in FIG. 6, where after etching of the walls of the frame we are left with a set of ceramic islands 703. Inhibiting the wall etching in a region defined for example with photo lithographic techniques, one obtains an extending connecting post 704. A conducting layer 705 is placed on the ceramic islands to be used both as a $2^{nd}$ casting frame and an electrode between the two final piezoelectric layers. FIG. 7*b* shows dents 706 that are etched into the layer 705 to form the casting frame for the $2^{nd}$ ceramic layer. The dents 706 are then filled with material and the casting frame walls 707 are removed between the ceramic islands just so that a continuous electrode 708 is found between the $1^{st}$ and $2^{nd}$ layers of ceramic islands (703/709) as shown in FIG. 7*c*.

For connections to the bottom electrode 702 one have inhibited the wall etching at 713, for example with photolithographic techniques, to produce the post 711 as a continuation of 704. Similarly, to connect to the intermediate layer 708 one have inhibited the wall etching at 714 to produce the post 712. The height of these posts can be increased as shown in the Figure, for example through electro-deposition of material. A third electrode 710 is placed on top of the $2^{nd}$ layer of ceramic islands.

FIG. 7*c* also shows fabrication from the substrate of an elastic layer 723 (for example with Si substrate) with the same function as 123 in FIGS. 1*c* and 2*b*, and a composite matching layer 722 according to the etching methods described in FIG. 5. 715 is then for example an outer, polymer load matching layer.

As the layer 705 has a certain thickness, it can be deposited onto the ceramic islands 703 without any material fill between the islands, providing lowest possible characteristic impedance of the composite. For thin electrodes 710 one can use low impedance polymer as fill between the islands 709 after the sintering of this ceramic, to provide continuous support of the electrode 710.

Figure 8:
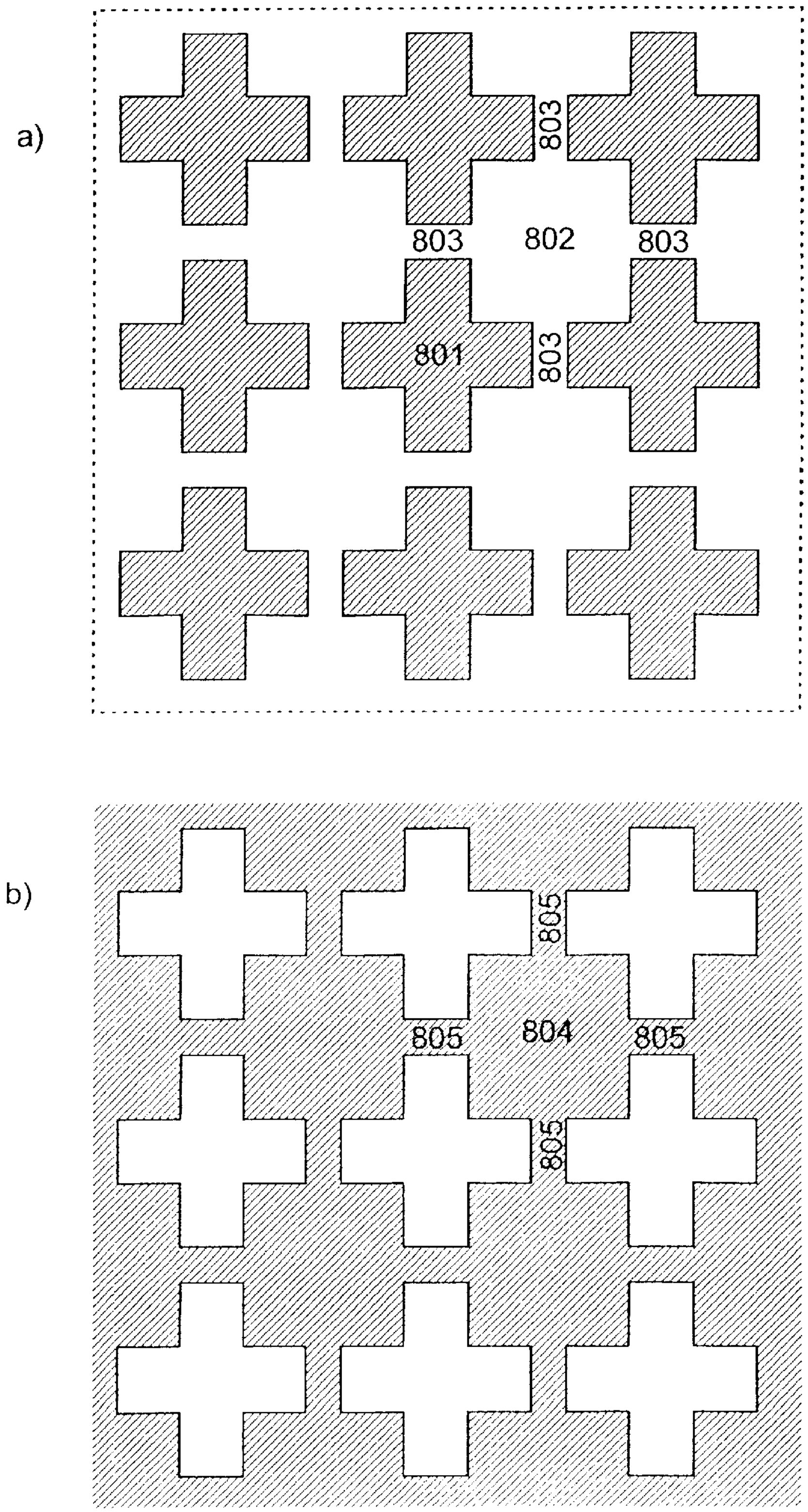
FIGS. 8*a* and 8*b*, show examples of manufacturing of ceramic multilayer composites with improved support of intermediate electrodes.

Improved support of the intermediate electrode 708 can be obtained by introducing bridges of ceramic between the islands, as illustrated in FIG. 8. In FIG. 8*a* a top-view of the casting frame is shown, where, 801 shows the walls of the frame and 802 shows the frame dents, which is reproduced in a repetitive pattern. The walls of the frame have openings 803 between the dents. Depositing ceramic material and etching of the casting frame walls, gives a ceramic structure as in FIG. 8*b*, where 804 shows the ceramic islands with bridges 805 between neighboring islands. Producing a 2nd layer on top of this layer as in FIG. 7, with the same shape of the casting frame as in FIG. 8*a*, the intermediate electrode is protected between the ceramic layers across the ceramic bridges. This provides stability of the electrode and also reduces the risk of breaking the continuity of the electrode with limited control of the etching of the walls of the casting frame.

FIG. 2*b* shows an example design according to the invention that provides more selective coupling of the layers of a transducer structure compared to that in FIG. 1*b*, 1*c*, or 2*a*. In this Figure, the electrodes 107 and 109 can via the RF switches 230 and 231 be coupled to transmitter amplifiers 232 and 233, or to receiver amplifiers 234 and 235, through electronic selection, while electrode 108 is connected to a common reference (e.g. ground). Electrical impedance matching can in the transmit mode be obtained by the units 236 and 237, and in the receive mode by the units 238 and 239. For sake of example, the electrical matching is in the Figure indicated by a parallel inductor and resistor, but other or more complex matching networks can be used, for example a series inductor, electronically selectable inductors for different frequency bands, or a network of inductors and capacitors.

In transmit position of RF-switches 230 and 231 and equal drive signals Tr1 and Tr2 of the amplifiers 232 and 233, the electrodes 107 and 109 will be driven with the same voltage signals, that corresponds to a parallel coupling of Port I and Port II to Port IV in the transmit mode. Grounding Tr2 with a drive signal on Tr1 only, one would transmit signals on Port I only, while grounding Tr1 with a drive signal on Tr2 only, one would transmit signals on Port II only. With some rearranging of the electrodes, switches and polarization one could also obtain a series coupling of the ports to Port III with similar techniques. One should also note that current output mode of the transmit amplifiers 232 and 233 with equal drive signals Tr1 and Tr2, would give series coupling of Port I and Port II with the structure as shown. By special selection of the drive signals Tr1 and Tr2, one can also simultaneously transmit a low frequency signal through Port IV and a high frequency signal through Port I or II.

Driving electrodes 107 and 109 with anti symmetric voltage drive signals, i.e. Tr2=−Tr1, one will get an anti parallel coupling of Port I and Port II where the drive voltages have opposite signs in relation to the polarization direction. This anti parallel coupling gives a port which enhances the transmit transfer function in FIG. 4*a* around 80 MHz. Similarly one can get an anti-serial coupling of Port I and Port II by using anti-symmetric drive signals Tr2=−Tr1 where the electrode 108 is not grounded, i.e. floats freely, which makes the currents into the two ports have opposite polarities. This anti-serial coupling similarly enhances the transmit transfer function in FIG. 4*a* around 80 MHz.

In receive position of the RF-switches 230 and 231, the output of the receiver amplifiers 234 and 235 reflects the signals on Port I and Port II, modified with the receiver input impedances. With zero input impedance of the receiver amplifiers (current amplifiers) one would get the receive transfer functions of the ports with shorted electrodes, which is the same as $H_{rt}(\omega)$ for each port. With high input impedance of the receiver amplifiers, one would get the receive transfer functions of the port with open electric ports. Good transfer functions are often obtained with a tuned receiver resistance exemplified as 238 and 239 in FIG. 2*b* (see comments above).

The outputs R1 and R2 of the receiver amplifiers 234 and 235 can conveniently be combined in the combination and filtering unit 240 to a new set of signals at a set of terminals 241, for example as $$R_k(\omega)=H_{k1}(\omega)R\mathbf{1}(\omega)+H_{k2}(\omega)R\mathbf{2}(\omega)\quad k=1,2,3, \tag{3}$$

where $\omega=2\pi f$ is the angular frequency and $H_{k1}(\omega)$ and $H_{k2}(\omega)$ are filters whose transfer functions are designed to obtain transfer functions from the pressure in the incident wave to the signals $R_k(\omega)$ in selected frequency bands. For widest possible receive band one can use the (m,N) filters defined as $$H_{c1}(\omega)=\frac{|H_{rt1}(\omega)|^{m-2}H_{rt1}^{*}(\omega)}{\left|H_{rt1}(\omega)\right|^{m}+\left|H_{rt2}(\omega)\right|^{m}+\max_{\omega}\{|H_{rt1}(\omega)|^{m}+|H_{rt2}(\omega)|^{m}\}/N} \tag{4}$$

$$H_{c2}(\omega)=\frac{|H_{rt2}(\omega)|^{m-2}H_{rt2}^{*}(\omega)}{\left|H_{rt1}(\omega)\right|^{m}+\left|H_{rt2}(\omega)\right|^{m}+\max_{\omega}\{|H_{rt1}(\omega)|^{m}+|H_{rt2}(\omega)|^{m}\}/N}$$

where $H_{rt1}(\omega)$ and $H_{rt2}(\omega)$ are the receive transfer functions of Port I and Port II, for example given as 404 and 405 in FIG. 4*b*. The full receive transfer function of this combination is $$\begin{aligned} H_c(\omega) &= H_{c1}(\omega)H_{rt1}(\omega)+H_{c2}(\omega)H_{rt2}(\omega) \\ &= \frac{1}{1+\max_{\omega}\{|H_{rt1}(\omega)|^{m}+|H_{rt2}(\omega)|^{m}\}/N\{|H_{rt1}(\omega)|^{m}+|H_{rt2}(\omega)|^{m}\}} \end{aligned} \tag{5}$$

Figure 4C:
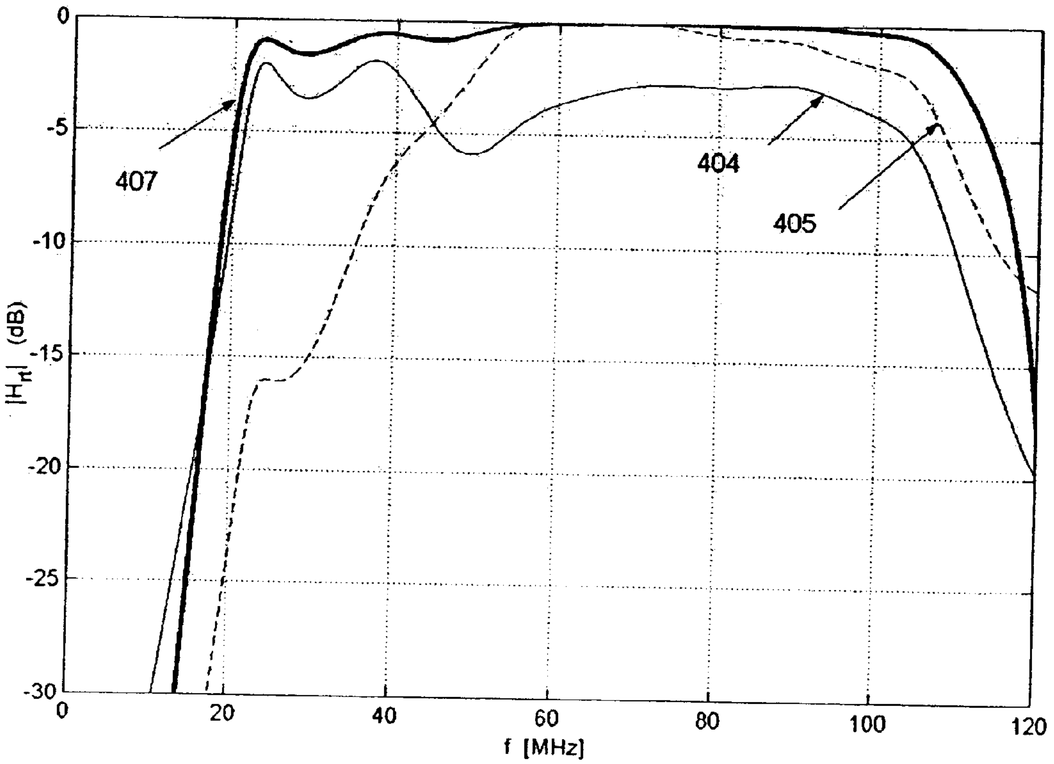

An example of $|H_c(\omega)|$ for m=2 and N=10 based on the same transducer structure as for FIGS. 4*a* and 4*b* is given as 407 in FIG. 4*c* together with 404 and 405 of FIG. 4*b* for comparison. We note that $H_c(\omega)$ covers a frequency range from 20–110 MHZ, i.e. a relative receive bandwidth of 138%. This wide receive bandwidth can then through further filtering be split into a 1st, 2nd, and 3rd harmonic component of the transmitted frequency band.

The transducer structure hence makes it possible to simultaneously transmit a low and a high frequency pulse with simultaneous reception in the two frequency bands to simultaneously display images obtained with a low and a high frequency pulse. The low frequency image is then used for wide range imaging while the high frequency image is used for high resolution imaging of close structures.

The structure is also well suited for utilizing the non-linear elastic properties of the tissue according to known methods, where by transmitting signals in one frequency band one can process the signal in sub-harmonic or higher harmonic bands, say $2^{nd}$, $3^{rd}$, or $4^{th}$ harmonic component of the transmitted band, for the imaging. Transmitting pulses in multiple frequency bands, one can filter out the received signal in bands where the frequencies are sums or differences of the frequencies in the transmitted bands, and selectively present images from frequencies in the transmitted bands or said sum and difference bands.

Thus, FIGS. 3 and 4 demonstrates that one with the embodiments of FIGS. 1 and 2 can obtain effective transducer operation with ceramic plates that are considerably thicker than the standard $\lambda/2$ operation for a transducer with $Z_B<Z_x$ or $\lambda/4$ operation for a transducer with $Z_B>Z_x$. This makes it possible to make transducers of layers of tape cast ceramic films with higher total thickness for a given frequency, than has previously been presented. This allows much higher frequency operation of such transducers than has previously been reported. Hence the transducer structures that are described, exemplifies the inventions ability to provide wideband and multiband operations in both transmit and receive modes with larger thicknesses of the composite ceramic plate than has previously been reported.

The design also makes it possible to use deposition of the films onto a substrate with a non piezoelectric ceramic layer close to the substrate that can be contaminated by the substrate during the sintering process. This allows the use of a wider class of substrates, in particular silicon that has a convenient characteristic impedance to be used as a load matching layer.

We note that while there have shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, the presented transfer functions are calculated with a selected set of material parameters and layer thicknesses, and adjustments and improvements in the transfer function characteristics can be obtained by adjustments of the parameters. One should note that according to the principle of the invention, the piezoelectric layers in these Figures could be given different thicknesses for tuning of the active frequency bands to desired requirements. One should also note that the transducer plates could be curved to provide focusing of the ultrasound beam, with negligible modifications in the transfer functions, or lenses could be placed in front of the plates to participate in the focusing of the ultrasound beam.

It is also expressly intended that all combinations of those elements and/or method steps which perform substantially the same function in substantially the same way to achieve the same results are within the scope of the invention. For example, one can group together many element transducers of the type shown into a transducer array according to well known principles. An array of such element transducers can also be obtained by cutting through the film layers with a laser or similar techniques, to divide the transducer into smaller elements grouped side by side to form an array radiating surface.

Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

Thus, while there have shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

We claim:

1. An ultrasound transducer for transmission and reception of ultrasound waves through a front radiating surface in acoustic contact with a load material, where in the thickness direction normal to the front surface the transducer comprises:

a transducer plate of thickness $L_x$, comprised of a stack of layers of films sintered together to the composite plate, the film materials having close to equal characteristic impedances so that thickness resonances of the transducer plate are determined by the total plate thickness, and a backing material of high ultrasound absorption such that reflected waves in the backing material can be neglected and having an impedance and to which the transducer plate is mounted, wherein at least one of the layers of the transducer plate is piezoelectric and has a thickness substantially smaller than the total thickness of the transducer plate, said piezoelectric layer being covered with conducting layers on both sides, and said conducting layers functioning as a $1^{st}$ electrode and a $2^{nd}$ electrode of an electric port to provide electromechanical coupling to thickness vibrations in the transducer in a $1^{st}$ frequency band, so that efficient electro-acoustic coupling of the transducer in the $1^{st}$ frequency band is obtained at frequencies at which the transducer plate is substantially thicker than half a wave length, said piezoelectric layer having a thickness of one of approximately half a wave length where the backing material has a low impedance and approximately a quarter of a wavelength where the backing material has a high impedance to obtain a thickness of the transducer plate substantially greater than half a wave length, so as to increase the mechanical stability of the plate during sintering and other handling processes and avoid contamination of said piezoelectric layer from substrate material during sintering.

2. An ultrasound transducer according to claim 1, wherein the transducer plate on the front side is acoustically connected to the load material through a load impedance matching section comprised of elastic load matching layers with selected thicknesses and characteristic impedances, and the transducer plate is connected acoustically on the back side to the backing material through one of a direct connection and a connection through a back matching section and said back matching section comprising elastic back matching layers with selected thicknesses and characteristic impedances, the backing material being absorbing so that reflected waves can be neglected.

3. An ultrasound transducer according to claim 2, wherein at least one of the front load matching layer and the back matching layer is made of an etchable, solid material, and wherein thin grooves are etched in the at least one matching layer, said grooves being filled with soft polymer material to provide a solid/polymer composites with composite characteristic impedances that are turnable by relative volume fill of the solid/polymer.

4. An ultrasound transducer according to claim 3, wherein the etchable solid comprises one of magnesium, aluminum, silicon, bismuth, beryllium, lead, cadmium, tin, gallium arsenide, germanium, titanium, zinc, zirconium, silver, copper, iron, gold, palladium, platinum and tungsten.

5. An ultrasound transducer according to claim 2, wherein the matching layers comprise low impedance matching layers deposited through one of sputtering and spin coating.

6. An ultrasound transducer according to claim 1, wherein said films comprise films manufactured by a tape-casting technique.

7. An ultrasound transducer according to claim 1, wherein said films comprise ceramic films deposited onto a substrate having an initial substrate thickness at least in front of the films that is reduced after film deposition through one of etching and grinding, so that the substrate thickness remaining after the thickness reduction forms a layer in one of a load impedance matching structure and a impedance matching structure.

8. An ultrasound transducer according to claim 7, wherein said substrate comprises semiconductor silicon (Si) that after the sintering is etched in front of the transducer plate to a thickness selected so that it functions as one of a load impedance matching layer and a back impedance matching layer.

9. An ultrasound transducer according to claim 7, wherein the front electrode is made of a dense material so that it isolates the ferroelectric ceramic material against contamination from the substrate material during sintering.

10. An ultrasound transducer according to claim 1, wherein the transducer plate comprises a thin back electrode with a low, close to negligible thickness wave propagation phase angle, and a layer of ceramic, ferroelectric film; covered on the front side by a conducting film with a non-negligible thickness wave propagation phase angle.

11. An ultrasound transducer according to claim 1, wherein a $3^{rd}$ electrode is located inside the transducer plate at one of an interface of the films in front of the $1^{st}$ and $2^{nd}$ electrodes and the front surface of the transducer plate, the layers between the $3^{rd}$ electrode and the $1^{st}$ and $2^{nd}$ electrodes being piezoelectric so as to form more electric ports for electro-acoustic coupling in frequency bands other than the $1^{st}$ frequency band.

12. An ultrasound transducer according to claims 1 or 11, wherein the $1^{st}$ electrode is located at the back face of the transducer plate.

13. An ultrasound transducer according to claim 11, wherein the $3^{rd}$ electrode comprises a film with a non-negligible thickness propagation phase angle that is part of the transducer plate, said $3^{rd}$ electrode being located at the front of the transducer plate.

14. An ultrasound transducer according to claim 13, wherein the $3^{rd}$ film is composed of one of silver (Ag) and a combination of silver (Ag) and palladium (Pd).

15. An ultrasound transducer according to claim 11, wherein the $3^{rd}$ electrode is located on the front face of the transducer plate, and has a characteristic impedance and thickness adjusted so that the electrode comprises part of a load impedance matching section of the transducer.

16. An ultrasound transducer according to claim 15, wherein the $3^{rd}$ electrode comprises one of magnesium, aluminum, and silicon.

17. An ultrasound transducer according to claims 13 or 15, wherein the $3^{rd}$ electrode is formed by electroplating.

18. An ultrasound transducer according to claims 13 or 15, wherein the $3^{rd}$ electrode has final thickness obtained by etching of the electrode material.

19. An ultrasound transducer according to claim 11, wherein the $1^{st}$ electrode is located at the backing face of the transducer plate, and the $3^{rd}$ electrode is located inside the transducer plate in front of the $2^{nd}$ electrode so that a film layer comprised of ceramic material is located in front of the $3^{rd}$ electrode.

20. An ultrasound transducer according to claim 19, further comprising an electrolytically deposited matching layer disposed close to the film layer at the front of the transducer plate.

21. An ultrasound transducer according to claim 4, wherein the layers of film comprise films deposited on a substrate having an initial thickness at least in front of the film that is reduced after film deposition through one of etching and grinding; so that the substrate thickness remaining after the thickness reduction forms a layer in one of a load impedance matching section and a back impedance matching section.

22. An ultrasound transducer according to claim 21, wherein the substrate is one of silicon (Si), a glass, a glass ceramics, and gallium arsenide (GaAs).

23. An ultrasound transducer according to claim 11, wherein at least two of the electric ports are combined into resultant ports through electrical connections of the electrodes.

24. An ultrasound transducer according to claim 1, wherein the film layers comprise ceramic layers comprising a ceramic composite formed by depositing a ceramic material in a casting frame and removing walls of the casting frame by one of chemical, optical, and electron etching to form ceramic islands of the composite.

25. An ultrasound transducer according to claim 1, wherein the film layers comprise ceramic layers formed as a ceramic composite by:

first establishing a casting frame one of on and in a substrate with at least walls of the frame being formed of etchable material, filling dents in the casting frame with ferroelectric ceramic material, and removing the walls of the casting frame by etching to form a matrix of ferroelectric ceramic elements.

26. An ultrasound transducer according to claim 25, wherein from the ceramic layers are further formed by filling voids created by the removing of the walls of the casting frame with a low characteristic impedance material; after sintering of the ceramic material.

27. An ultrasound transducer according to claim 25, wherein the casting frame is formed by first establishing an electrode material on the substrate, and then building the walls of the casting frame by electroplating walls of etchable material in a pattern defined by photo-lithography.

28. An ultrasound transducer according to claim 25, wherein the casting frame is formed by first establishing on the substrate an electrode material having a thickness greater than a desired ultimate thickness of the ceramic film, and then etching the dents of the casting frame to define an electrode in a pattern defined through photo-lithography.

29. An ultrasound transducer according to claims 27 or 28, wherein a connection to the electrode material on the substrate from the top of the film is defined by shielding small regions of the casting frame wall against further etching photo-lithography.

30. A multi electric port ultrasound transducer with at least two piezoelectric layers according to claim 11, wherein the piezoelectric layers comprise a ceramic composite formed by depositing the ceramic material in a casting frame and removing walls of the casting frame by one of chemical, optical and electron etching to form ceramic islands of the composite.

31. A multi electric port ultrasound transducer with at least two piezoelectric layers according to claim 30, wherein the transducer plate is formed by:

a) forming a 1$^{st}$ casting frame is according to claim 25, b) filling the casting frame with ferroelectric ceramic material, c) covering the surface of the ceramic material with an etchable electrode material into which a 2$^{nd}$ casting frame is formed according to one of claim 27 and claim 28, d) filling the 2$^{nd}$ casting frame with the ferroelectric ceramic material, and repeating the steps (a), (b) and (C) until all of the layers are formed to thereby, produce a transducer plate comprised of multiple composite piezoelectric layers on top of each other with intermediate electrodes to form a transducer with multiple electric ports.

32. A multi electric port ultrasound transducer with at least two piezoelectric layers according to claim 31, wherein the walls of the casting frames have openings at the same locations for each layer; so that bridges are formed between the ceramic islands to support and cover the electrodes between the ceramic islands to improve stability and continuity of the intermediate electrodes.

33. A multi-electric port ultrasound transducer with at least two piezoelectric layers according to claim 31, wherein electric connections from a surface of the transducer plate to deeper electrodes within the transducer plate are defined by inhibiting etching of the casting frame walls at selected locations.

34. An ultrasound transducer array composed of a plurality of element transducers each according to claims 1 or 11, and arranged to form an array radiating surface for electronic forming of an output ultrasound beam.

35. An ultrasound transducer array according to claim 34, wherein each of the plural element transducers is formed according to claim 7, and wherein separation of the transducer elements is defined by a casting frame with etchable walls, with at least some of the walls of the frame defining an interelement separation, voids in the frame being filled with ceramic material, and the walls being removed by etching.

36. An ultrasound transducer array according to claim 35, wherein the casting frame is formed by etching the voids in the substrate, and a pattern of the casting frame voids and walls being defined by photo-lithography.

37. An ultrasound transducer array according to claim 35, wherein the casting frame is formed by first applying an electrode layer onto the substrate, and the walls of the casting frame are formed by electroplating etchable material onto the electrode.

38. An ultrasound transducer array according to claim 35, wherein the casting frame is formed by first applying an electrode layer onto the substrate with a thickness greater than the thickness of the films, and the voids of the casting frame being defined by etching into the electrode layer.

39. An ultrasound transducer array according to claim 34, wherein separation of the elements is defined by cutting a complete, sintered film transducer into a plurality of smaller elements by one of laser cutting and etching.

40. An ultrasound transducer array according to claim 34, wherein the elements comprise ceramic composites formed by depositing the ceramic material in a casting frame and removing walls of the casting frame by one of chemical, optical and electron etching to form ceramic islands of the composite.

41. An ultrasound transceiver system comprising an ultrasound transducer according to claim 11, wherein one electrode is connected to a common ground, and the other electrodes are connected to separate transmitter amplifiers and receiver amplifiers.

42. An ultrasound transceiver system according to claim 41, wherein in transmitting mode the electrodes are connected to the transmitter amplifiers so that selection of the electric ports during transmission is effected by selecting drive signals on the transmitter amplifiers.

43. An ultrasound transceiver system according to claim 41, wherein in receiving mode the electrodes are connected to the receiver amplifiers so that the outputs of the receiver amplifiers represent different electric receiver ports.

44. An ultrasound transceiver system according to claim 43, wherein signals from individual receiver amplifiers are combined to obtain one of a wide band transfer function and transfer functions in multiple frequency bands.

45. An ultrasound array transceiver system composed of a set of element transceiver systems each according to claim 41, the transducer elements of the element transceiver systems forming a transducer array radiating surface for electronic forming of an output ultrasound beam wherein by selecting drive signals on the element ports a pulsed electronically formed beam can be transmitted with frequency components in one of selectable and multiple frequency bands, and through delays of element port signals, with an electronically formed receive beam can be received with receive signals in one of selectable and multiple frequency bands.

46. An ultrasound imaging system comprising one of an ultrasound transducer and a transducer array with transducer elements according to claims 1 or 11, and operable for transmitting a pulse with frequencies in at least two frequency bands.

47. An ultrasound imaging system according to claim 46 and operable for receiving scattered signals in multiple frequency bands where the receive signal is filtered to at least two separate signals for at least two frequency bands that are part of the transmitted bands for one of selectively and simultaneously processing of the filter output signals, for one of selectively and simultaneously presenting images based on the filter output signals, wherein low frequency bands are used for deep overview imaging and high frequency bands are used for higher resolution imaging at shorter depths.

48. An ultrasound imaging system according to claim 46 and operable for receiving scattered signals in multiple frequency bands where the receive signal is filtered to at least one signal in a frequency band where the frequencies of the frequency band are one of sums and differences between frequencies in transmitted frequency bands, and for processing at least the filtered signal for display of an image based on the filtered signal.

49. An ultrasound imaging system according to claim 47, wherein scattered signals in at least two frequency bands are used to estimate absorption in tissue.

50. An ultrasound imaging system according to claim 48, wherein a scattered signal in at least the filtered band is used to assess non-linear elastic coefficients of tissue.

51. An ultrasound imaging system comprising one of an ultrasound transducer and an array of ultrasound transducer elements according to claims 1 or 11, and operable for transmitting an ultrasound pulse in one frequency band, receiving a signal in both the one frequency band and one of a higher harmonic component and a sub-harmonic component of the one frequency band, and separating the received signal in the transmitted frequency band and in the one of a sub-harmonic component band and the a higher harmonic band for one of selectively and simultaneously presenting an image based on received signal components in one of the transmitted frequency band and one of the higher harmonic component and the sub-harmonic component of the transmitted frequency band.

52. An ultrasound transducer according to claim 1, wherein the transducer plate comprises a front electrode, and a back electrode with characteristic impedance close to the piezoelectric film and of a thickness selected so that the back electrode participates in defining a resonance of the transducer plate, the back electrode being acoustically connected to the backing material.

53. An ultrasound transducer according to claim 52, wherein said films comprise ferromagnetic ceramic films deposited onto a substrate, and wherein the front electrode is made of a dense material so that it isolates the ferroelectric ceramic material against contamination from the substrate material during sintering.

54. An ultrasound transducer array according to claim 34, wherein the plural transducer elements are constructed in accordance with one of claim 51, claim 52 and claim 53.

55. An ultrasound transducer array according to claim 54, wherein each the plural element transducers comprises a front electrode and a back electrode, wherein the front electrode and the piezoelectric layer are continuous across the whole array, and the back electrode comprises a separate single electrode for each element transducer, the front electrode providing a common ground electrode and the back electrodes being adapted for receiving individual element signals.

* * * * *